(12) United States Patent
Hahn et al.

(10) Patent No.: US 9,120,771 B2
(45) Date of Patent: Sep. 1, 2015

(54) AZETIDINE DERIVATIVE AND ANTIDEPRESSANT COMPOSITION INCLUDING THE SAME

(75) Inventors: Hoh-Gyu Hahn, Seoul (KR); Kee-Dal Nam, Seoul (KR); Min-soo Han, Seoul (KR); Young-Hue Han, Seoul (KR); Chi-Man Song, Seoul (KR); Dong-Yun Shin, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/239,890

(22) PCT Filed: Sep. 4, 2012

(86) PCT No.: PCT/KR2012/007076
§ 371 (c)(1),
(2), (4) Date: Feb. 20, 2014

(87) PCT Pub. No.: WO2013/036015
PCT Pub. Date: Mar. 14, 2013

(65) Prior Publication Data
US 2014/0171402 A1 Jun. 19, 2014

(30) Foreign Application Priority Data
Sep. 5, 2011 (KR) .................. 10-2011-0089820

(51) Int. Cl.
C07D 403/06 (2006.01)
C07D 205/04 (2006.01)
(52) U.S. Cl.
CPC ............ *C07D 403/06* (2013.01); *C07D 205/04* (2013.01)
(58) Field of Classification Search
CPC .................................................. C07D 205/04
See application file for complete search history.

(56) References Cited

U.S. PATENT DOCUMENTS

2006/0293299 A1 12/2006 Baker et al.
2009/0069284 A1 3/2009 Baker et al.

FOREIGN PATENT DOCUMENTS

| KR | 10-2006-0019587 A | 3/2006 |
|---|---|---|
| WO | 2005/077897 A1 | 8/2005 |
| WO | 2006/028961 A2 | 3/2006 |
| WO | 2009/016048 A1 | 2/2009 |
| WO | 2009/109743 A1 | 9/2009 |
| WO | 2010/059390 A1 | 5/2010 |
| WO | 2010/059393 A1 | 5/2010 |
| WO | 2010/138589 A1 | 12/2010 |
| WO | 2011/103196 A1 | 8/2011 |

OTHER PUBLICATIONS

Marks et al., Triple Reuptake Inhibitors: The Next Generation of Antidepressants. Current Neuropharmacology, 2008, 6, 338-343.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Suppporting information of Han et al., Exploration of Novel 3-Substituted Azetidine Derivatives As Triple Reuptake Inhibitors. Journal of Medicinal Chemistry, 2012, 55, 8188-8192).*
T. Alescio, "Effect of a proline analogue, azetidine-2-carboxylic acid, on the morphogenesis *in vitro* of mouse embryonic lung," *Journal of Embryology and Experimental Morphology*, vol. 29, No. 2, 1973, pp. 439-451.
M. Feledziak et al., "SAR and LC/MS Studies of β-Lactamic Inhibitors of Human Fatty Acid Amide Hydrolase (*h*FAAH): Evidence of a Nonhydrolytic Process," *Journal of Medicinal Chemistry*, vol. 54, 2011, pp. 6812-6823.
Y. Han et al., "Exploration of Novel 3-Substituted Azetidine Derivatives As Triple Reuptake Inhibitors," *Journal of Medicinal Chemistry*, vol. 55, 2012, pp. 8188-8192.
Database Registry[online], Chemical Abstract Service, Columbus, Ohio, US, "3-Azetidinemethanol,, Alpha., 1-Dimethyl-" Jul. 26, 2011.
European Search Report dated Jan. 15, 2015, of the corresponding European Patent Application No. 12829591.2.

* cited by examiner

*Primary Examiner* — Michael Barker
*Assistant Examiner* — Po-Chih Chen
(74) *Attorney, Agent, or Firm* — Goldilocks ZONE IP Law

(57) ABSTRACT

The present invention relates to an azetidine derivative or a pharmaceutically acceptable salt thereof, and an antidepressant agent or a composition for the prevention or treatment of psychiatric disorders including the same. The azetidine derivative is useful as a triple reuptake inhibitor capable of inhibiting reuptake of the neurotransmitters, dopamine, serotonin, and norepinephrine at the same time.

9 Claims, No Drawings

AZETIDINE DERIVATIVE AND ANTIDEPRESSANT COMPOSITION INCLUDING THE SAME

CROSS-REFERENCE TO RELATED APPLICATIONS

This application is a U.S. national stage application of PCT/KR2012/007076 filed Sep. 4, 2012 and claims foreign priority benefit of Korean Patent Application No. 10-2011-0089820 filed Sep. 5, 2011 in the Korean Intellectual Property Office, the contents of both of which are incorporated herein by reference.

BACKGROUND OF THE INVENTION

1. Field of the Invention

The present invention relates to a compound (triple reuptake inhibitor) capable of inhibiting reuptake of the neurotransmitters, dopamine, serotonin, and norepinephrine at the same time, and an antidepressant including the same.

2. Description of the Related Art

Depression, namely, depressive disorder means a disease that is characterized by loss of interest and sadness as major symptoms and causes various cognitive, emotional, and physical symptoms, leading to impairment of normal function. It has been estimated that the lifetime prevalence of depressive disorder is 15%, and in particular, 25% in women. Depressive disorder is a serious illness causing emotional, cognitive, physical and behavioral changes.

The etiology of depression is complex, resulting from interactions of various genes, and epigenetic, genetic, and environmental factors, rather than a single cause. Consequently, impairment in feelings occurs, leading to emotional disorders.

Compounds currently used for depression exhibit great therapeutic effects on other symptoms caused by a pathophysiologic substance, such as memory loss, desynchronization, and pain, as well as emotional impairment in depression.

Drugs typically used for other major mental or neurological disorders show their efficacy through a variety of neural mechanisms distributed throughout the brain. Similarly, pharmacological, anatomical, and neuropsychiatric approaches to alleviation of depression cannot be made to exhibit efficacy through one mechanism of action.

Since the antituberculosis drug iproniazid was proved to show an anti-depressant effect as a monoamine oxidase inhibitor (MAOIs), modern antidepressants have been actively developed. In the early 1950s, an antihistamine, chlorpromazine was developed as an antipsychotic agent, and its therapeutic effect on schizophrenia was proved. Similarly, since imipramine was developed as an antihistamine by Geigy Drug Co. in Switzerland, 1955, active development of antidepressants has begun. These discoveries brought about development of tricyclic antidepressants (TCA), and many TCAs such as nortriptyline, doxepin, clomipramine or the like have come into use, in addition to amitriptyline or desipramine having a modified tricyclic structure.

Later, second- and third-generation antidepressants have been developed, and tetracyclic compounds such as maprotiline and amoxapine that are similar in the structure and efficacy were commercialized in the early 1980s, which are also called heterocyclics.

In the 1980s, one of the selective serotonin reuptake inhibitors (SSRIs), Prozac was developed and used as an effective therapeutic agent. However, it has been reported that Prozac causes anticholinergic side effects of dry mouth, constipation, urinary retention, blurred vision, impotence or the like, acts on the cardiovascular system to considerably affect blood pressure, pulse, cardiac conduction or the like, blocks 1-adrenergic receptors to cause orthostatic hypotension, and has antihistamine effects that explain its sedative action.

Current antidepressant agents include selective serotonin reuptake inhibitors, serotonin and norepinephrine reuptake inhibitors, selective norepinephrine reuptake inhibitors, dopamine and norepinephrine reuptake inhibitors (DNRI), noradrenergic and specific serotonergic antidepressants (NaSSA), serotonin-antagonists/serotonin reuptake inhibitors (SARI), selective serotonin reuptake enhancers (SSRE) or the like.

These antidepressant agents currently used in the treatment show low remission rates. Thus, it is difficult to achieve sufficient therapeutic effects by using these drugs. For this reason, the antidepressant market is expected to reduce. In order to overcome the low remission rate, it is required to develop a new concept of therapeutic agent.

Representative side effects of the current therapeutic antidepressants are sexual dysfunction and weight gain, and development of new antidepressants that are able to overcome these side effects is expected to open a new market.

One of other major problems is that the current therapeutic antidepressants have a lag-time of several weeks to several months until its onset of action after drug administration. Improvement of efficacy by reducing the lag-time is also an important issue in the development of antidepressants.

For proper selection and efficacy improvement of antidepressant agents, personalized therapy must be provided through the investigations of new biomarkers for major depressive disorder.

Owing to their mechanism of action, antidepressant agents can be also applied to other neuropsychiatric disorders such as neurogenic pain, bipolar disorder or the like. Thus, the development of related studies makes it possible to achieve external extension of the antidepressant market.

SUMMARY OF THE INVENTION

Accordingly, the present inventors have made many efforts to develop a drug for the improvement and/or treatment of depression, which has fewer side effects and improved efficacy by reducing a lag-time until its onset of action. As a result, they synthesized a novel compound capable of inhibiting reuptake of dopamine, serotonin, and norepinephrine at the same time, thereby completing the present invention.

Therefore, one object of the present invention is to provide a compound capable of inhibiting reuptake of dopamine, serotonin, and norepinephrine at the same time.

Another object of the present invention is to provide an antidepressant composition including the above compound as an active ingredient.

Still another object of the present invention is to provide a composition including the above compound as an active ingredient for the prevention and/or treatment of neuropsychiatric disorders such as neurogenic pain and bipolar disorder.

DETAILED DESCRIPTION OF THE PREFERRED EMBODIMENTS

The present invention relates to a compound (triple reuptake inhibitor) capable of inhibiting reuptake of the neurotransmitters, dopamine, serotonin, and norepinephrine at the same time, and an antidepressant agent including the same. The compound is useful in the prevention and/or treatment of neuropsychiatric disorders such as neurogenic pain and bipolar disorder as well as depression.

First, one aspect of the present invention relates to an azetidine derivative having the structure of the following Chemical Formula 1:

[Chemical Formula 1]

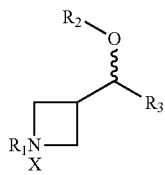

wherein $R_1$ may be hydrogen or a methyl group, $R_2$ may be hydrogen, a naphthyl group, a straight- or branched-chain alkyl group having 1 to 5 carbon atoms, for example, 1 to 3 carbon atoms, —$COC_6H_5$, or a substituted or unsubstituted phenyl group or benzyl group, in which one or more hydrogen atoms, preferably, one or two hydrogen atom(s) of the substituted phenyl group or benzyl group is/are each independently substituted with one selected from the group consisting of halogen (e.g., fluorine or chlorine), a straight- or branched-chain alkyl group having 1 to 3 carbon atoms (e.g., methyl), and trifluoromethoxy, $R_3$ may be selected from the group consisting of a straight- or branched-chain alkyl group having 1 to 5 carbon atoms, a tetrazole group, a cyclic alkyl group having 3 to 10 carbon atoms, preferably 3 to 6 carbon atoms, and a substituted or unsubstituted aromatic compound having 6 to 12 carbon atoms, preferably 6 to 10 carbon atoms (e.g., phenyl or naphthyl), in which one or more hydrogen atoms, preferably, one or two hydrogen atom(s) of the substituted aromatic compound is/are each independently substituted with one selected from the group consisting of halogen (e.g., fluorine or chlorine) and a straight- or branched-chain alkyl group having 1 to 3 carbon atoms (e.g., methyl), and X may be hydrogen halide, for example, hydrogen chloride or may not exist.

In the azetidine derivative having the structure of Chemical Formula 1 of one specific embodiment.

$R_1$ may be hydrogen, $R_2$ may be hydrogen, a naphthyl group, a straight- or branched-chain alkyl group having 1 to 3 carbon atoms, —$COC_6H_5$, or a substituted or unsubstituted phenyl group or benzyl group, in which one or two hydrogen atom(s) of the substituted phenyl group or benzyl group is/are each independently substituted with one selected from the group consisting of fluorine, chlorine, methyl, and trifluoromethoxy, $R_3$ may be selected from the group consisting of a straight- or branched-chain alkyl group having 3 to 5 carbon atoms, a tetrazole group, a cyclic alkyl group having 3 to 6 carbon atoms, and a substituted or unsubstituted phenyl and naphthyl group, in which one or two hydrogen atom(s) of the substituted phenyl or naphthyl group is/are each independently substituted with one selected from the group consisting of fluorine, chlorine, and methyl, X may be hydrogen chloride or may not exist.

Because the azetidine derivative has the pharmacological characteristics as described below, another aspect of the present invention provides a pharmaceutical composition including the azetidine derivative or a pharmaceutically acceptable salt thereof as an active ingredient.

Meanwhile, depression is known to be caused by a deficiency or an imbalance of the neurotransmitters, dopamine, serotonin, and norepinephrine in the synapses. There are many methods for treating the deficiency of the neurotransmitters in the synapses. For example, the problem due to neurotransmitter deficiency can be solved by inhibiting reuptake of the secreted endogenous neurotransmitters to maintain high levels of neurotransmitters in the synapses. This treatment method has fewer side effects and thus is effectively used as a depression therapy.

Meanwhile, currently available antidepressant agents exhibit antidepressant effects by inhibiting the reuptake of each of the representative neurotransmitters, dopamine, serotonin, and norepinephrine or by reuptake of two types of the neurotransmitters among them. However, there have been no drugs capable of inhibiting reuptake of three representative neurotransmitters, dopamine, serotonin, and norepinephrine at the same time. The drug capable of inhibiting reuptake of the representative neurotransmitters, dopamine, serotonin, and norepinephrine at the same time by action of a single compound has the advantage of remarkably reducing side effects of the drug.

As confirmed in the following Table 2, the azetidine derivative of the present invention has an excellent effect of inhibiting reuptake of serotonin, norepinephrine, and dopamine at the same time, and thus it is useful in the treatment of depression. The azetidine derivative of the present invention is a single compound to inhibit reuptake of three types of neurotransmitters at the same time, and thus it is advantageous in that side effects are remarkably reduced and depression can be more effectively treated.

Accordingly, still another aspect relates to an antidepressant agent, namely, a composition for the prevention and/or treatment of depression, including the azetidine derivative having the structure of Chemical Formula 1 or the pharmaceutically acceptable salt thereof as an active ingredient. Still another aspect relates to a method for preventing and/or treating depression, including the step of administering the azetidine derivative having the structure of Chemical Formula 1 or the pharmaceutically acceptable salt thereof at a therapeutically effective amount to a patient in need of prevention or treatment of depression. The method for preventing and/or treating depression may further include the step of identifying the patient in need of prevention and/or treatment of depression prior to the administration step. Still another aspect relates to use of the azetidine derivative having the structure of Chemical Formula 1 or the pharmaceutically acceptable salt thereof in the prevention and/or treatment of depression, or use thereof in the preparation of a composition for the prevention and/or treatment of depression.

Further, inhibition of the reuptake of serotonin, norepinephrine, and dopamine is useful for the prevention and/or treatment of psychiatric disorders such as neurogenic pain, bipolar disorder, schizophrenia, mood disorders, sleep disorders, anxiety disorder, attention deficit hyperactive disorder (ADHD), eating disorder or the like.

Accordingly, still another aspect relates to a composition for the prevention and/or treatment of psychiatric disorders, including the azetidine derivative having the structure of Chemical Formula 1 or the pharmaceutically acceptable salt thereof as an active ingredient. Still another aspect relates to a method for preventing and/or treating a depression, including the step of administering the azetidine derivative having the structure of Chemical Formula 1 or the pharmaceutically acceptable salt thereof at a therapeutically effective amount to a patient in need of prevention or treatment of psychiatric disorders. The method for preventing and/or treating psychiatric disorders may further include the step of identifying the patient in need of prevention and/or treatment of psychiatric disorders prior to the administration step. Still another aspect relates to use of the azetidine derivative having the structure of Chemical Formula 1 or the pharmaceutically acceptable salt thereof in the prevention and/or treatment of psychiatric disorders or depression, or use thereof in the preparation of a composition for the prevention and/or treatment of psychiatric disorders or depression.

The psychiatric disorder may be selected from the group consisting of neurogenic pain, bipolar disorder, schizophrenia, mood disorders, sleep disorders, anxiety disorder, attention deficit hyperactive disorder (ADHD), eating disorder or the like.

The content of the active ingredient azetidine derivative in the composition for the prevention and/or treatment of antidepressant or psychiatric disorders of the present invention may be generally in the range of 0.1 to 99% by weight, but it is preferable that the preferred content is properly adjusted depending on the administration method of the composition, the patient's status, and the desired effects. Further, the administration dose or the therapeutically effective dose of the present invention is preferably determined, considering the patient's age, sex, and status, the absorption rate of the active ingredient in the body, the inactivity rate and concomitant medications. The daily dose may be 0.001 mg/kg (body weight) to 100 mg/kg (body weight), and preferably 0.001 mg/kg (body weight) to 50 mg/kg (body weight), based on the active ingredient, but is not limited thereto. The dose may be given once a day or in 2 divided dose a day.

The patient of the present invention who is subjected to prevention or treatment, or administration may be a mammal, and preferably a human.

In the composition of the present invention, the azetidine derivative is included alone, or other drug and/or a pharmaceutically acceptable carrier and/or excipient may be further included therein. The carrier or excipient usable in the composition of the present invention may be properly selected according to the formulation, and typical diluents, fillers, extenders, wetting agents, disintegrants, and/or surfactants may be used.

The pharmaceutical composition may be formulated into various oral or parenteral administration forms. For example, it may be prepared into any formulation for oral administration, such as tablets, pills, hard/soft capsules, liquid solutions, suspensions, emulsions, syrups, granules, elixirs or the like. These formulations for oral administration may include, in addition to the active ingredient, a pharmaceutically acceptable carrier such as diluents (e.g., lactose, dextrose, sucrose, mannitol, sorbitol, cellulose and/or glycerin) or lubricants (e.g., silica, talc, stearic acid and magnesium or calcium salts thereof, and/or polyethylene glycol) according to the typical composition of each formulation.

Further, if the formulation for oral administration is a tablet, it may include binding agents such as magnesium aluminum silicate, starch paste, gelatin, tragacanth, methyl cellulose, sodium carboxymethylcellulose and/or polyvinylpyrrolidone, and if desired, disintegrators, e.g., starches, agar, alginic acid or sodium salts thereof, effervescent mixtures and/or adsorption agents, colorants, flavoring agents, sweeteners or the like.

The pharmaceutical composition may be prepared into a formulation for parenteral administration, which can be administered by parenteral route such as subcutaneous, intravenous, intramuscular or intrasternal injection. In order to prepare a formulation for parenteral administration, the active ingredient, namely, the derivative of Chemical Formula 1 or the pharmaceutically acceptable salt thereof ought to be mixed with stabilizers or buffers in water to make solutions or suspensions, which may be formulated in a unit dosage form of ampoules or vials.

Further, the pharmaceutical composition may be sterilized or may further include adjuvants, such as preserving, stabilizing, wetting or emulsifying agents, salts for regulating the osmotic pressure and/or buffers. In addition, the composition may also include other therapeutically useful substances, and the composition may be prepared according to conventional mixing, granulating or coating methods.

The azetidine derivative of the present invention has an excellent inhibitory effect on reuptake of serotonin, norepinephrine, and dopamine, and has fewer side effects than the conventional inhibitors and a remarkably short lag-time until its onset of action after administration. Therefore, it can be effectively used in antidepressant agents and/or in the improvement and/or treatment of psychiatric disorder.

Hereinafter, the present invention will be described in more detail with reference to the following Examples. However, these are provided for illustrative purposes only, and the scope of the present invention should not be limited to these Examples.

Example 1

Synthesis of tertiary-butyl 3-(hydroxymethyl)azetidine-1-carboxylate

[Reaction Scheme 1a]

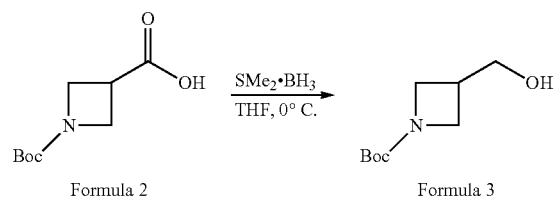

Borane dimethyl sulfide complex (4.5 mL, 15.0 mmol) was slowly added to 1-(tertiary butoxycarbonyl)azetidine-3-carboxylic acid (1.0 g, 5.0 mmol) dissolved in a distilled tetrahydrofuran solution (20 mL) at 0° C., and the mixture was stirred at the same temperature for 4 hours. Thereafter, 1N HCl aqueous solution (70 mL) was slowly added at 0° C., and the mixture was stirred at room temperature for 30 minutes. The reaction mixture was extracted with ethyl acetate (3*30 mL), and the organic layer was washed with a saturated sodium chloride solution and distilled water once, respectively and dried over anhydrous magnesium sulfate. The solvent was removed by reduced pressure evaporation to obtain the desired compound tertiary butyl 3-(hydroxymethyl)azetidine-1-carboxylate.

Yield: 98%, oily liquid $^{1}$H NMR (300 MHz, CDCl$_{3}$-d$_{3}$) δ 1.42 (s, 9H, CO$_{2}$C(CH$_{3}$)$_{3}$), 2.70-2.66 (m, 1H, CH(CH$_{2}$)$_{2}$), 3.418 (dd, 1H, OH), 3.71-3.65 (m, 4H, CH(CH$_{2}$)$_{2}$), 3.99-3.93 (m, 2H, CH$_{2}$OH).

Example 2

Synthesis of tertiary butyl 3-formyl azetidine-1-carboxylate

[Reaction Scheme 1b]

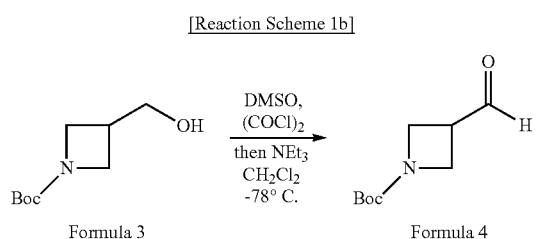 [SMILES: CC(C)(C)OC(=O)N1CC(CO)C1 ; CC(C)(C)OC(=O)N1CC(C=O)C1]

Dimethyl sulfoxide (1.1 mL, 15.0 mmol) was slowly added to 20 mL of oxalyl chloride (1.3 mL, 15.0 mmol) dissolved in distilled methylene chloride solution at −78° C., and the mixture was stirred at the same temperature for 30 minutes. Then, tertiary butyl 3-(hydroxymethyl)azetidine-1-carboxylate (900 mg, 5.0 mmol) was added thereto, and the mixture was stirred at the same temperature for 3 hours. Thereafter, triethylamine (6.0 mL, 45.0 mmol) was slowly added at −78° C., and the mixture was stirred for 1 hour. The reaction mixture was extracted with methylene chloride (3*30 mL), and the organic layer was washed with a saturated sodium chloride solution and distilled water once, respectively and dried over anhydrous magnesium sulfate. The solvent was removed by reduced pressure evaporation to obtain a light yellow liquid, which was purified by flash chromatography (n-hexane:ethyl acetate (1:1, v/v)). The product was identified as a single compound by TLC (thin layer chromatography); n-hexane:ethyl acetate (1:1, v/v)).

Yield: 85%, yellow oily liquid $^{1}$H NMR (300 MHz, CDCl$_{3}$-d$_{3}$) δ 1.44 (s, 9H, CO$_{2}$C(CH$_{3}$)$_{3}$), 3.39-3.30 (m, 1H, CH(CH$_{2}$)$_{2}$), 4.11-4.05 (m, 4H, CH(CH$_{2}$)$_{2}$), 9.85 (s, 1H, CHO).

Example 3

Synthesis of tertiary butyl 3-((3,4-dichlorophenyl)(hydroxy)methyl)azetidine-1-carboxylate

[Reaction Scheme 1c]

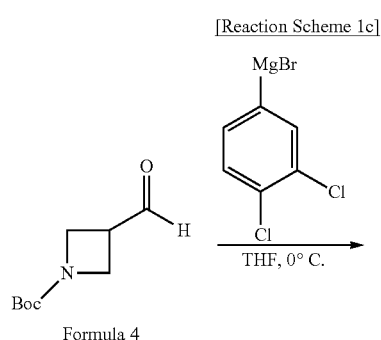

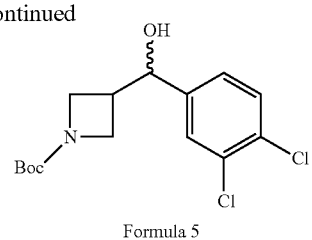

Formula 5

1 molar solution (22 mL, 21.1 mmol) of (3,4-dichlorophenyl)magnesium bromide dissolved in the tetrahydrofuran solution was cooled to 0° C., and tertiary butyl 3-formyl azetidine-1-carboxylate (1.3 g, 7.02 mmol) was slowly added thereto at 0° C., and the mixture was stirred at the same temperature for 3 hours. Thereafter, a saturated ammonium chloride aqueous solution (15 mL) was slowly added at 0° C., and the mixture was stirred at room temperature for 1 hour. The reaction mixture was extracted with methylene chloride (3*30 mL), and the organic layer was washed with a saturated sodium chloride solution and distilled water once, respectively and dried over anhydrous magnesium sulfate. The solvent was removed by reduced pressure evaporation to obtain a yellow liquid, which was purified by flash chromatography (n-hexane:ethyl acetate (4:1, v/v)). The product was identified as a single compound by TLC (n-hexane:ethyl acetate (4:1, v/v)).

Yield: 68%, white solid, melting point: 254° C.

$^{1}$H NMR (300 MHz, CDCl$_{3}$-d$_{3}$) δ 1.44 (s, 9H, CO$_{2}$C(CH$_{3}$)$_{3}$), 2.85-2.74 (m, 1H, CH(CH$_{2}$)$_{2}$), 2.99-2.98 (d, 1H, OH), 3.97-3.66 (m, 4H, CH(CH$_{2}$)$_{2}$), 4.79-4.75 (dd, 1H, CH), 7.48-7.17 (m, 3H, ArH).

Example 4

Synthesis of tertiary butyl 3-((3,4-dichlorophenyl)(phenoxy)methyl)azetidine-1-carboxylate

[Reaction Scheme 1d]

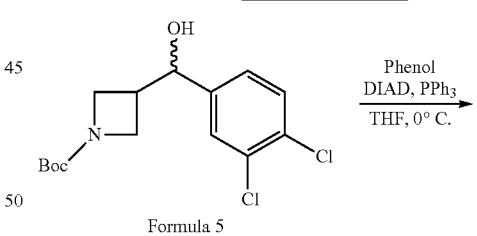

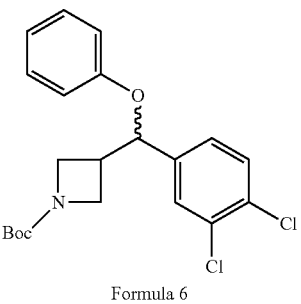

Formula 6

Phenol (0.1 mL, 0.903 mmol) was added to 10 mL of tertiary butyl 3-((3,4-dichlorophenyl)(hydroxy)methyl)azetidine-1-carboxylate (150 mg, 0.452 mmol) and triphenylphosphine (237 mg, 0.903 mmol) dissolved in distilled tetrahydrofuran solution, and diisopropyl azocarboxylate (0.18 mL, 0.903 mmol) was slowly added at 0° C., and the mixture was stirred at room temperature for one day. The solvent of the reaction mixture was removed by reduced pressure evaporation to obtain a yellow liquid, which was purified by flash chromatography (n-hexane:ethyl acetate (4:1, v/v)). The product was identified as a single compound by TLC (n-hexane:ethyl acetate (4:1, v/v)).

Yield: 89%, oily liquid $^1$H NMR (300 MHz, CDCl$_3$-d$_3$) δ 1.44 (s, 9H, CO$_2$C (C$\underline{H_3}$)$_3$), 2.99-2.89 (m, 1H, C$\underline{H}$(CH$_2$)$_2$), 4.15-3.75 (m, 4H, CH(C$\underline{H_2}$)$_2$), 5.13 (d, 1H, J=7.5 Hz, CH), 7.45-6.78 (m, 8H, ArH).

Example 5

Synthesis of tertiary butyl 3-((3,4-dichlorophenyl)(methoxy)methyl)azetidine-1-carboxylate

[Reaction Scheme 1e]

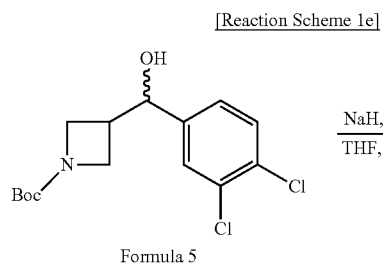

Formula 5

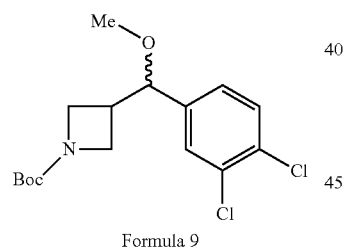

Formula 9

Methyl iodide (0.1 mL, 1.20 mmol) was slowly added to 15 mL of tertiary butyl 3-((3,4-dichlorophenyl)(hydroxy)methyl)azetidine-1-carboxylate (200 mg, 0.602 mmol) and NaH (44 mg, 1.20 mmol) dissolved in a distilled methylene chloride solution at 0° C., and the mixture was stirred for 4 hours. Thereafter, purified water (3 ml) was added thereto, and the mixture was stirred at room temperature for 30 minutes. The reaction mixture was extracted with methylene chloride (3*30 mL), and the organic layer was washed with a saturated sodium chloride solution and distilled water once, respectively and dried over anhydrous magnesium sulfate. The solvent was removed by reduced pressure evaporation to obtain a colorless liquid, which was purified by flash chromatography (n-hexane:ethyl acetate (4:1, v/v)). The product was identified as a single compound by TLC (n-hexane:ethyl acetate (4:1, v/v)).

Yield: 78%, oily liquid $^1$H NMR (300 MHz, CDCl$_3$-d$_3$) δ 1.43 (s, 9H, CO$_2$C (C$\underline{H_3}$)$_3$), 2.76-2.64 (m, 1H, C$\underline{H}$(CH$_2$)$_2$), 3.22 (s, 3H, OCH$_3$), 4.00-3.56 (m, 4H, CH(C$\underline{H_2}$)$_2$), 4.18 (d, 1H, J=8.4 Hz, CH), 7.45-7.12 (m, 3H, ArH).

Example 6

Synthesis of tertiary butyl 3-((benzoyloxy)(3,4-dichlorophenyl)methyl)azetidine-1-carboxylate

[Reaction Scheme 1f]

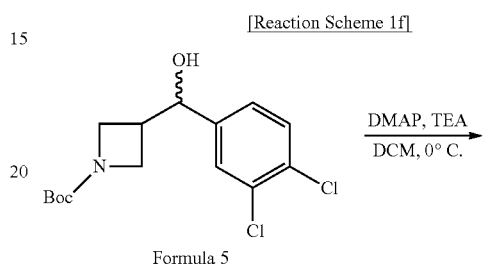

Formula 5

Formula 10

Benzoyl chloride (0.1 mL, 1.20 mmol) and DMAP (5 mg, 0.03 mmol) were slowly added to 15 mL of tertiary butyl 3-((3,4-dichlorophenyl)(hydroxy)methyl)azetidine-1-carboxylate (100 mg, 0.302 mmol) and triethylamine (0.07 mL, 0.482 mmol) dissolved in the distilled methylene chloride solution at 0° C., and the mixture was stirred at room temperature for one day. The reaction mixture was extracted with methylene chloride (3*30 mL), and the organic layer was washed with a 1 N HCl aqueous solution and distilled water once, respectively and dried over anhydrous magnesium sulfate. The solvent was removed by reduced pressure evaporation to obtain a colorless liquid, which was purified by flash chromatography (n-hexane:ethyl acetate (2:1, v/v)). The product was identified as a single compound by TLC (n-hexane:ethyl acetate (2:1, v/v)).

Yield: 88%, oily liquid $^1$H NMR (300 MHz, CDCl$_3$-d$_3$) δ 1.43 (s, 9H, CO$_2$C (C$\underline{H_3}$)$_3$), 3.17-3.05 (m, 1H, C$\underline{H}$(CH$_2$)$_2$), 4.14-3.69 (m, 4H, CH(C$\underline{H_2}$)$_2$), 6.10-6.08 (d, 1H, J=7.5 Hz, CH), 8.06-7.25 (m, 8H, ArH).

Example 7

Synthesis of 3-((3,4-dichlorophenyl)(phenoxy)methyl)azetidine hydrochloride (KHG26767)

[Reaction Scheme 1g]

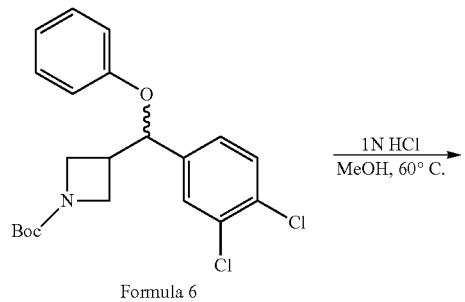

Formula 6

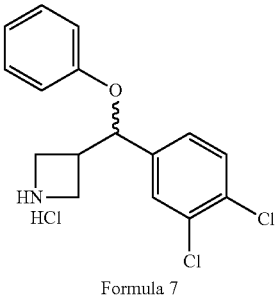

Formula 7

1N HCl (3 mL) was added to 10 mL of tertiary butyl 3-((3,4-dichlorophenyl)(phenoxy)methyl)azetidine-1-carboxylate (150 mg, 0.352 mmol) dissolved in a methanol solution, and heated to reflux at 60° C. for one day. Thereafter, the solvent of the reaction mixture was removed by reduced pressure evaporation to obtain the title compound.

Yield: 97%, white solid, melting point: 175° C.

$^1$H NMR (300 MHz, DMSO-d$_6$) δ 3.28-3.21 (m, 1H, C<u>H</u>(CH$_2$)$_2$), 4.01-3.84 (m, 4H, CH(C<u>H$_2$</u>)$_2$), 5.80-5.78 (d, J=6.6 Hz, 1H, CH), 7.69-6.90 (m, 8H, ArH), 9.41 (br(s), 2H, NH, HCl).

Example 8

Synthesis of 3-((3,4-dichlorophenyl)(phenoxy)methyl)-1-methylazetidine (KHG26906)

[Reaction Scheme 1h]

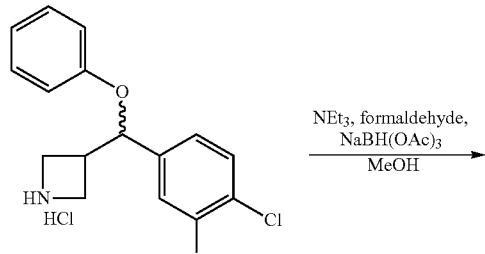

Formula 7

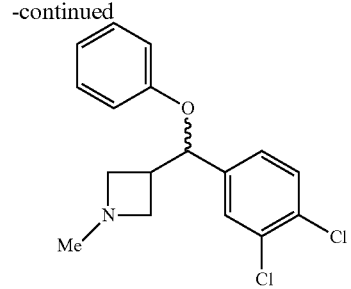

Formula 8

Triethylamine (0.2 mL, 1.313 mmol) was added to 20 mL of 3-((3,4-dichlorophenyl)(phenoxy)methyl)azetidine hydrochloride (300 mg, 0.870 mmol) dissolved in a methanol solution, and the mixture was stirred at room temperature for 1 hour. 37% formaldehyde aqueous solution (0.3 ml, 3.50 mmol) and acetic acid (0.2 ml, 3.50 mmol) were added to the reaction mixture, and NaBH(OAc)$_3$ (742 mg, 3.50 mmol) was added thereto, followed by stirring for one day. Thereafter, 1 mL of 1 N NaOH was added thereto, and the mixture was stirred for 30 minutes. The organic layer was washed with distilled water, and the organic layer was adjusted to pH 7 using a 1 N NaOH aqueous solution, and extracted with methylene chloride (3*30 mL) and dried over anhydrous magnesium sulfate. The solvent was removed by reduced pressure evaporation to obtain a colorless liquid, which was purified by flash chromatography (methylene chloride:methanol (9:1, v/v)). The product was identified as a single compound by TLC (methylene chloride:methanol (9:1, v/v)).

Yield: 67%, oily liquid

The following compounds were synthesized according to the same method

KHG26749 azetidine-3-yl(phenyl)methanol hydrochloride

Yield 77%; Melting Point 223° C.;

$^1$H NMR (300 MHz, DMSO-d$_6$) δ 3.03-2.93 (m, 1H, C<u>H</u>(CH$_2$)$_2$), 3.95-3.73 (m, 4H, CH(C<u>H$_2$</u>)$_2$), 4.80-4.77 (d, J=6.3 Hz, 1H, CH), 7.30-7.14 (m, 5H, ArH), 9.18 and 9.31 (2br(s), 2H, NH, HCl).

KHG26750

3-(methoxy(phenyl)methyl)azetidine hydrochloride

Yield 50%; Melting Point 228° C.;

$^1$H NMR (300 MHz, DMSO-d$_6$) δ 3.02-2.97 (m, 1H, C<u>H</u>(CH$_2$)$_2$), 3.21 (s, 3H, OC<u>H$_3$</u>), 3.95-3.71 (m, 4H, CH(C<u>H$_2$</u>)$_2$), 4.53-4.50 (d, J=7.5 Hz, 1H, CH), 7.46-7.33 (m, 5H, ArH), 9.26 (br(s), 2H, NH, HCl).

KHG26751

3-(ethoxy(phenyl)methyl)azetidine hydrochloride

Yield 31%; Melting Point 205° C.; $^1$H NMR (300 MHz, DMSO-d$_6$) δ 1.15-1.06 (t, J=7.2 Hz, 3H, OCH$_2$C<u>H$_3$</u>), 3.03-2.92 (m, 1H, C<u>H</u>(CH$_2$)$_2$), 3.93-3.86 (q, J=6.9 Hz, 2H, OC<u>H$_2$</u>CH$_3$), 3.78-3.67 (m, 2H, CH(C<u>H$_2$</u>)$_2$), 3.35-3.30 (m, 2H, CH(C<u>H$_2$</u>)$_2$), 4.60-4.58 (d, J=7.2 Hz, 1H, CH), 7.41-7.30 (m, 5H, ArH), 9.16 (br(s), 2H, NH, HCl).

KHG26752 azetidine-3-ly(4-chlorophenyl)methanol hydrochloride

Yield 96%; Melting Point 248° C.; $^1$H NMR (300 MHz, DMSO-d$_6$) δ 3.02-2.94 (m, 1H, C<u>H</u>(CH$_2$)$_2$), 3.86-3.78 (m, 4H, CH(C<u>H$_2$</u>)$_2$), 4.81-4.79 (d, J=5.7 Hz, 1H, CH), 6.05 (br(s), 1H, OH) 7.42-7.34 (2d, 4H, ArH), 9.02 and 9.21 (2br(s), 2H, NH, HCl).

KHG26753

3-((4-chlorophenyl)(methoxy)methyl)azetidine hydrochloride

Yield 85%; Melting Point 281° C.; $^1$H NMR (300 MHz, DMSO-d$_6$) δ 3.03-2.90 (m, 1H, C$\underline{H}$(CH$_2$)$_2$), 3.17 (s, 3H, OC$\underline{H}_3$), 3.90-3.67 (m, 4H, CH(C$\underline{H}_2$)$_2$), 4.54-4.52 (d, J=7.2 Hz, 1H, CH), 7.47-7.33 (2d, 4H, ArH), 9.30 (br(s), 2H, NH, HCl).

KHG26754

3-((4-chlorophenyl)(ethoxy)methyl)azetidine hydrochloride

Yield 65%; Melting Point 190° C.; $^1$H NMR (300 MHz, DMSO-d$_6$) δ 1.15-1.07 (t, J=7.2 Hz, 3H, OCH$_2$C$\underline{H}_3$), 3.01-2.88 (m, 1H, C$\underline{H}$(CH$_2$)$_2$), 3.37-3.30 (q, J=6.9 Hz, 2H, OC$\underline{H}_2$CH$_3$), 3.80-3.63 (m, 2H, CH(C$\underline{H}_2$)$_2$), 3.89-3.86 (m, 2H, CH(C$\underline{H}_2$)$_2$), 4.64-4.62 (d, J=7.2 Hz, 1H, CH), 7.46-7.33 (2d, 4H, ArH), 9.17 (br(s), 2H, NH, HCl).

KHG26755 azetidine-3-ly(3,4-dichlorophenyl)methanol hydrochloride

Yield 75%; Melting Point 186° C.; $^1$H NMR (300 MHz, DMSO-d$_6$) δ 3.06-2.98 (m, 1H, C$\underline{H}$(CH$_2$)$_2$), 3.84-3.80 (m, 4H, CH(C$\underline{H}_2$)$_2$), 4.83-4.81 (d, J=4.8 Hz, 1H, CH), 6.19 (br(s), 1H, OH) 7.62-7.32 (m, 3H, ArH), 8.99 and 9.20 (2br(s), 2H, NH, HCl

KHG26756

3-((3,4-dichlorophenyl)(methoxy)methyl)azetidine hydrochloride

Yield 81%; Melting Point 109° C.; $^1$H NMR (300 MHz, DMSO-d$_6$) δ 3.09-2.98 (m, 1H, C$\underline{H}$(CH$_2$)$_2$), 3.26 (s, 3H, OC$\underline{H}_3$), 4.17-3.88 (m, 4H, CH(C$\underline{H}_2$)$_2$), 4.47-4.45 (d, J=7.2 Hz, 1H, CH), 7.46-7.15 (m, 3H, ArH), 9.29 (br(s), 2H, NH, HCl).

KHG26757

3-((3,4-dichlorophenyl)(ethoxy)methyl)azetidine hydrochloride

Yield 76%; Melting Point 156° C.; $^1$H NMR (300 MHz, DMSO-d$_6$) δ 1.16-1.11 (t, J=6.9 Hz, 3H, OCH$_2$C$\underline{H}_3$), 3.05-2.95 (m, 1H, C$\underline{H}$(CH$_2$)$_2$), 3.39-3.30 (q, J=6.9 Hz, 2H, OC$\underline{H}_2$CH$_3$), 3.82-3.67 (m, 2H, CH(C$\underline{H}_2$)$_2$), 3.88-3.86 (m, 4H, CH(C$\underline{H}_2$)$_2$), 4.67-4.64 (d, J=7.2 Hz, 1H, CH), 7.67-7.32 (m, 3H, ArH), 9.14 (br(s), 2H, NH, HCl).

KHG26758

1-(azetidine-3-ly)-2-phenyl ethanol hydrochloride

Yield 55%; Melting Point 243° C.; $^1$H NMR (300 MHz, DMSO-d$_6$) δ 2.65-2.58 (m, 2H, CH(OH)C$\underline{H}_2$C$_6$H$_5$), 2.81-2.71 (m, 1H, C$\underline{H}$(CH$_2$)$_2$), 3.85-3.70 (m, 4H, CH(C$\underline{H}_2$)$_2$), 5.37-5.36 (d, J=4.5 Hz, 1H, CH), 7.33-7.18 (m, 3H, ArH), 9.14 and 8.80 (2br(s), 2H, NH, HCl).

KHG26759

3-(methoxy(ortho-tolyl)methyl)azetidine hydrochloride

Yield 82%; Melting Point 220° C.; $^1$H NMR (300 MHz, DMSO-d$_6$) δ 2.34 (s, 3H, ArC$\underline{H}_3$) 3.12-3.02 (m, 1H, C$\underline{H}$(CH$_2$)$_2$), 3.16 (s, 3H, OC$\underline{H}_3$), 3.96-3.68 (m, 4H, CH(C$\underline{H}_2$)$_2$), 4.74-4.72 (d, J=6 Hz, 1H, CH), 7.25-7.20 (m, 4H, ArH), 9.33 and 9.24 (2br(s), 2H, NH, HCl).

KHG26765

3-(methoxy(ortho-tolyl)methyl)azetidine hydrochloride

Yield 33%; Melting Point 200° C.; $^1$H NMR (300 MHz, DMSO-d$_6$) δ 3.27-3.17 (m, 1H, C$\underline{H}$(CH$_2$)$_2$), 4.05-3.78 (m, 4H, CH(C$\underline{H}_2$)$_2$), 5.72-5.70 (d, J=7.2 Hz, 1H, CH), 7.42-6.86 (m, 10H, ArH), 9.35 (br(s), 2H, NH, HCl).

KHG26766

3-((4-chlorophenyl)(phenoxy)methyl)azetidine hydrochloride

Yield 52%; Melting Point 191° C.; $^1$H NMR (300 MHz, DMSO-d$_6$) δ 3.27-3.17 (m, 1H, C$\underline{H}$(CH$_2$)$_2$), 4.00-3.78 (m, 4H, CH(C$\underline{H}_2$)$_2$), 5.75-5.73 (d, J=6.9 Hz, 1H, CH), 7.43-6.88 (m, 9H, ArH), 9.30 (br(s), 2H, NH, HCl).

KHG26767

3-((3,4-dichlorophenyl)(phenoxy)methyl)azetidine hydrochloride

Yield 57%; Melting Point 175° C.; $^1$H NMR (300 MHz, DMSO-d$_6$) δ 3.28-3.21 (m, 1H, C$\underline{H}$(CH$_2$)$_2$), 4.01-3.84 (m, 4H, CH(C$\underline{H}_2$)$_2$), 5.80-5.78 (d, J=6.6 Hz, 1H, CH), 7.69-6.90 (m, 8H, ArH), 9.41 (br(s), 2H, NH, HCl).

KHG26768

3-((benzyloxy)(phenyl)methyl)azetidine hydrochloride

Yield 82%; Melting Point 185° C.; $^1$H NMR (300 MHz, DMSO-d$_6$) δ 3.10-3.02 (m, 1H, C$\underline{H}$(CH$_2$)$_2$), 3.92-3.73 (m, 4H, CH(C$\underline{H}_2$)$_2$), 4.41-4.29 (dd, 2H, J=11.7 Hz, OC$\underline{H}_2$Ar), 4.68-4.66 (d, J=7.2 Hz, 1H, CH), 7.45-7.30 (m, 10H, ArH), 9.19 and 9.06 (2br(s), 2H, NH, HCl).

KHG26769

3-((benzyloxy)(4-chlorophenyl)methyl)azetidine hydrochloride

Yield 88%; Melting Point 184° C.; $^1$H NMR (300 MHz, DMSO-d$_6$) δ 3.10-3.00 (m, 1H, C$\underline{H}$(CH$_2$)$_2$), 3.96-3.68 (m, 4H, CH(C$\underline{H}_2$)$_2$), 4.41-4.30 (dd, 2H, J=11.7 Hz, OC$\underline{H}_2$Ar), 4.72-4.70 (d, J=7.5 Hz, 1H, CH), 7.50-7.28 (m, 9H, ArH), 9.16 (br(s), 2H, NH, HCl).

KHG26770

3-((benzyloxy)(3,4-dichlorophenyl)methyl)azetidine hydrochloride

Yield 72%; Melting Point 128° C.; $^1$H NMR (300 MHz, DMSO-d$_6$) δ 3.14-3.04 (m, 1H, C$\underline{H}$(CH$_2$)$_2$), 3.92-3.74 (m, 4H, CH(C$\underline{H}_2$)$_2$), 4.44-4.34 (dd, 2H, J=11.7 Hz, OC$\underline{H}_2$Ar), 4.77-4.74 (d, J=7.2 Hz, 1H, CH), 7.67-7.35 (m, 8H, ArH), 9.31 and 9.14 (2br(s), 2H, NH, HCl).

KHG26771 azetidine-3-yl(phenyl)methyl benzoate hydrochloride

Yield 69%; Melting Point 215° C.; $^1$H NMR (300 MHz, DMSO-d$_6$) δ 3.45-3.40 (m, 1H, C$\underline{H}$(CH$_2$)$_2$), 4.11-3.84 (m, 4H, CH(C$\underline{H}_2$)$_2$), 6.18-6.16 (d, J=7.2 Hz, 1H, CH), 8.13-7.31 (m, 10H, ArH), 9.44 and 9.23 (2br(s), 2H, NH, HCl).

KHG26772 azetidine-3-ly(4-chlorophenyl)methyl benzoate hydrochloride

Yield 54%; Melting Point 201° C.; $^1$H NMR (300 MHz, DMSO-d$_6$) δ 3.47-3.39 (m, 1H, C$\underline{H}$(CH$_2$)$_2$), 4.14-3.84 (m, 4H, CH(C$\underline{H}_2$)$_2$), 6.19-6.17 (d, J=7.2 Hz, 1H, CH), 8.13-7.43 (m, 9H, ArH), 9.31 (br(s), 2H, NH, HCl).

KHG26773 azetidine-3-ly(3,4-dichlorophenyl)methyl benzoate hydrochloride

Yield 57%; Melting Point 204° C.; $^1$H NMR (300 MHz, DMSO-d$_6$) δ 3.50-3.34 (m, 1H, C$\underline{H}$(CH$_2$)$_2$), 4.16-3.87 (m, 4H, CH(C$\underline{H}_2$)$_2$), 6.18-6.16 (d, J=6.9 Hz, 1H, CH), 8.15-7.44 (m, 8H, ArH), 9.26 (br(s), 2H, NH, HCl).

KHG26774

3-((3,4-dichlorophenyl)(ortho-tolyloxy)methyl)azetidine hydrochloride

Yield 60%; Melting Point 194° C.; $^1$H NMR (300 MHz, DMSO-d$_6$) δ 1.99 (s, 3H, ArC$\underline{H}_3$), 3.35-3.28 (m, 1H, C$\underline{H}$(CH$_2$)$_2$), 4.08-3.88 (m, 4H, CH(C$\underline{H}_2$)$_2$), 5.75-5.73 (d, J=6.3 Hz, 1H, CH), 7.68-6.72 (m, 7H, ArH), 9.32 and 9.22 (2br(s), 2H, NH, HCl).

KHG26775

3-((3,4-dichlorophenyl)(meta-tolyloxy)methyl)azetidine hydrochloride

Yield 51%; Melting Point 200° C.; $^1$H NMR (300 MHz, DMSO-d$_6$) δ 2.25 (s, 3H, ArC$\underline{H}_3$), 3.33-3.23 (m, 1H, C$\underline{H}$(CH$_2$)$_2$), 4.07-3.86 (m, 4H, CH(C$\underline{H}_2$)$_2$), 5.81-5.79 (d, J=6.6 Hz, 1H, CH), 7.71-6.76 (m, 7H, ArH), 9.44 (br(s), 2H, NH, HCl).

KHG26776

3-((3,4-dichlorophenyl)(para-tolyloxy)methyl)azetidine hydrochloride

Yield 99%; Melting Point 193° C.; $^1$H NMR (300 MHz, DMSO-d$_6$) δ 2.18 (s, 3H, ArC$\underline{H_3}$), 3.33-3.23 (m, 1H, C$\underline{H}$(CH$_2$)$_2$), 4.04-3.88 (m, 4H, CH(C$\underline{H_2}$)$_2$), 5.66-5.64 (d, J=6.6 Hz, 1H, CH), 7.66-6.83 (m, 7H, ArH), 9.10 (br(s), 2H, NH, HCl).

KHG26779

3-((3,4-dichlorophenyl)(propoxy)methyl)azetidine hydrochloride

Yield 58%; Melting Point 151° C.; $^1$H NMR (300 MHz, DMSO-d$_6$) δ 0.89-0.83 (t, 3H, J=7.2 Hz, OCH$_2$CH$_2$C$\underline{H_3}$), 1.57-1.50 (q, 2H, J=7.2 Hz, OCH$_2$C$\underline{H_2}$CH$_3$), 3.04-2.96 (m, 1H, C$\underline{H}$(CH$_2$)$_2$), 3.27-3.23 (m, 2H, OC$\underline{H_2}$CH$_2$CH$_3$), 3.89-3.71 (m, 4H, CH(C$\underline{H_2}$)$_2$), 4.64-4.62 (d, J=6.3 Hz, 1H, CH), 7.67-7.31 (m, 3H, ArH), 9.14 (br(s), 2H, NH, HCl).

KHG26780

3-((3,4-dichlorophenyl)(2-fluorophenoxy)methyl)azetidine hydrochloride

Yield 86%; Melting Point 224° C.; $^1$H NMR (300 MHz, DMSO-d$_6$) δ 3.26-3.23 (m, 1H, C$\underline{H}$(CH$_2$)$_2$), 4.05-3.82 (m, 4H, CH(C$\underline{H_2}$)$_2$), 5.87-5.85 (d, J=6.3 Hz, 1H, CH), 7.72-6.98 (m, 7H, ArH), 9.24 (br(s), 2H, NH, HCl).

KHG26781

3-((3,4-dichlorophenyl)(3-fluorophenoxy)methyl)azetidine hydrochloride

Yield 20%; Melting Point 218° C.; $^1$H NMR (300 MHz, DMSO-d$_6$) δ 3.26-3.24 (m, 1H, C$\underline{H}$(CH$_2$)$_2$), 4.00-3.83 (m, 4H, CH(C$\underline{H_2}$)$_2$), 5.80-5.78 (d, J=5.1 Hz, 1H, CH), 8.20-6.74 (m, 7H, ArH), 9.20 (br(s), 2H, NH, HCl).

KHG26782

3-((3,4-dichlorophenyl)(4-fluorophenoxy)methyl)azetidine hydrochloride

Yield 25%; Melting Point 210° C.; $^1$H NMR (300 MHz, DMSO-d$_6$) δ 3.28-3.20 (m, 1H, C$\underline{H}$(CH$_2$)$_2$), 4.06-3.80 (m, 4H, CH(C$\underline{H_2}$)$_2$), 5.70-5.67 (d, J=6.6 Hz, 1H, CH), 7.68-6.96 (m, 7H, ArH), 9.18 (br(s), 2H, NH, HCl).

KHG26783

3-((2-chlorophenoxy)(3,4-dichlorophenyl)methyl)azetidine hydrochloride

Yield 35%; Melting Point 197° C.; $^1$H NMR (300 MHz, DMSO-d$_6$) δ 3.35-3.30 (m, 1H, C$\underline{H}$(CH$_2$)$_2$), 4.06-3.85 (m, 4H, CH(C$\underline{H_2}$)$_2$), 5.93-5.91 (d, J=7.2 Hz, 1H, CH), 7.70-6.93 (m, 7H, ArH), 9.30 and 9.20 (2br(s), 2H, NH, HCl).

KHG26784

3-((3-chlorophenoxy)(3,4-dichlorophenyl)methyl)azetidine hydrochloride

Yield 58%; Melting Point 169° C.; $^1$H NMR (300 MHz, DMSO-d$_6$) δ 3.27-3.20 (m, 1H, C$\underline{H}$(CH$_2$)$_2$), 4.01-3.79 (m, 4H, CH(C$\underline{H_2}$)$_2$), 5.83-5.81 (d, J=6.3 Hz, 1H, CH), 7.69-6.91 (m, 7H, ArH), 9.32 (br(s), 2H, NH, HCl).

KHG26785

3-((4-chlorophenoxy)(3,4-dichlorophenyl)methyl)azetidine hydrochloride

Yield 44%; Melting Point 201° C.; $^1$H NMR (300 MHz, DMSO-d$_6$) δ 3.27-3.22 (m, 1H, C$\underline{H}$(CH$_2$)$_2$), 4.06-3.81 (m, 4H, CH(C$\underline{H_2}$)$_2$), 5.73-5.71 (d, J=6.6 Hz, 1H, CH), 7.66-6.83 (m, 7H, ArH), 9.10 (br(s), 2H, NH, HCl).

KHG26786

3-((3,4-dichlorophenyl)(2-(trifluoromethoxy)phenoxy)methyl)azetidine hydrochloride Yield 92%; Melting Point 225° C.; $^1$H NMR (300 MHz, DMSO-d$_6$) δ 3.44-3.38 (m, 1H, C$\underline{H}$(CH$_2$)$_2$), 4.05-3.84 (m, 4H, CH(C$\underline{H_2}$)$_2$), 6.05-6.03 (dd, 1H, CH), 7.72-7.03 (m, 7H, ArH), 9.47 (br(s), 2H, NH, HCl).

KHG26787

3-((3,4-dichlorophenyl)(3-(trifluoromethoxy)phenoxy)methyl)azetidine hydrochloride Yield 77%; Melting Point 208° C.; $^1$H NMR (300 MHz, DMSO-d$_6$) δ 3.30-3.22 (m, 1H, C$\underline{H}$(CH$_2$)$_2$), 4.07-3.80 (m, 4H, CH(C$\underline{H_2}$)$_2$), 5.85-5.83 (d, J=6.3 Hz, 1H, CH), 7.71-6.91 (m, 7H, ArH), 9.30 (br(s), 2H, NH, HCl).

KHG26788

3-((3,4-dichlorophenyl)(4-(trifluoromethoxy)phenoxy)methyl)azetidine hydrochloride Yield 28%; Melting Point 217° C.; $^1$H NMR (300 MHz, DMSO-d$_6$) δ 3.28-3.23 (m, 1H, C$\underline{H}$(CH$_2$)$_2$), 4.02-3.82 (m, 4H, CH(C$\underline{H_2}$)$_2$), 5.77-5.75 (d, J=6.3 Hz, 1H, CH), 7.69-6.81 (m, 7H, ArH), 9.24 (br(s), 2H, NH, HCl).

KHG26789

3-((3,4-dichlorophenyl)(3,4-difluorophenoxy)methyl)azetidine hydrochloride

Yield 61%; Melting Point 240° C.; $^1$H NMR (300 MHz, DMSO-d$_6$) δ 3.31-3.21 (m, 1H, C$\underline{H}$(CH$_2$)$_2$), 4.05-3.81 (m, 4H, CH(C$\underline{H_2}$)$_2$), 5.80-5.78 (d, J=6.3 Hz, 1H, CH), 7.71-7.05 (m, 6H, ArH), 9.33 (br(s), 2H, NH, HCl).

KHG26790

3-((3,4-dichlorophenoxy)(3,4-dichlorophenyl)methyl)azetidine hydrochloride

Yield 12%; Melting Point 208° C.; $^1$H NMR (300 MHz, DMSO-d$_6$) δ 3.30-3.26 (m, 1H, C$\underline{H}$(CH$_2$)$_2$), 4.03-3.84 (m, 4H, CH(C$\underline{H_2}$)$_2$), 5.80-5.79 (dd, 1H, CH), 7.70-6.95 (m, 6H, ArH), 9.19 (br(s), 2H, NH, HCl).

KHG26791

3-(ethoxy(naphthalene-2-yl)methyl)azetidine hydrochloride

Yield 67%; Melting Point 205° C.; $^1$H NMR (300 MHz, DMSO-d$_6$) δ 1.18-1.13 (t, 3H, J=7.2 Hz, OCH$_2$C$\underline{H_3}$), 3.13-3.05 (m, 1H, C$\underline{H}$(CH$_2$)$_2$), 3.43-3.35 (q, 2H, J=7.2 Hz, OC$\underline{H_2}$CH$_3$), 3.96-3.69 (m, 4H, CH(C$\underline{H_2}$)$_2$), 4.79-4.76 (d, J=7.8 Hz, 1H, CH), 7.96-7.44 (m, 7H, ArH), 9.24 (br(s), 2H, NH, HCl).

KHG26792

3-(naphthalene-2-yl(propoxy)methyl)azetidine hydrochloride

Yield 69%; Melting Point 223° C.; $^1$H NMR (300 MHz, DMSO-d$_6$) δ 0.90-0.81 (t, 3H, J=7.2 Hz, OCH$_2$CH$_2$C$\underline{H_3}$), 1.61-1.50 (q, 2H, J=7.2 Hz, OCH$_2$C$\underline{H_2}$CH$_3$), 3.17-3.06 (m, 1H, C$\underline{H}$(CH$_2$)$_2$), 3.28-3.25 (m, 2H, OC$\underline{H_2}$CH$_2$CH$_3$), 3.96-3.76 (m, 4H, CH(C$\underline{H_2}$)$_2$), 4.75-4.73 (d, J=7.5 Hz, 1H, CH), 7.95-7.42 (m, 7H, ArH), 9.15 (br(s), 2H, NH, HCl).

KHG26793

3-(naphthalene-2-yl(phenoxy)methyl)azetidine hydrochloride

Yield 69%; Melting Point 218° C.; $^1$H NMR (300 MHz, DMSO-d$_6$) δ 3.31-3.22 (m, 1H, C$\underline{H}$(CH$_2$)$_2$), 4.12-3.88 (m, 4H, CH(C$\underline{H_2}$)$_2$), 5.87-5.85 (d, J=6.9 Hz, 1H, CH), 8.24-6.84 (m, 12H, ArH), 9.35 (br(s), 2H, NH, HCl).

KHG26794

3-((2-fluorophenoxy)(naphthalene-2-yl)methyl)azetidine hydrochloride

Yield 79%; Melting Point 211° C.; $^1$H NMR (300 MHz, DMSO-d$_6$) δ 3.44-3.39 (m, 1H, C$\underline{H}$(CH$_2$)$_2$), 4.15-3.85 (m, 4H, CH(C$\underline{H_2}$)$_2$), 5.96-5.93 (d, J=7.8 Hz, 1H, CH), 7.96-6.85 (m, 11H, ArH), 9.10 (br(s), 2H, NH, HCl).

KHG26795

3-((3-fluorophenoxy)(naphthalene-2-yl)methyl)azetidine hydrochloride

Yield 78%; Melting Point 216° C.; $^1$H NMR (300 MHz, DMSO-d$_6$) δ 3.33-3.23 (m, 1H, C$\underline{H}$(CH$_2$)$_2$), 4.13-3.83 (m, 4H, CH(C$\underline{H_2}$)$_2$), 5.91-5.89 (d, J=6.9 Hz, 1H, CH), 7.95-6.69 (m, 11H, ArH), 9.25 (br(s), 2H, NH, HCl).

KHG26796
3-((4-fluorophenoxy)(naphthalene-2-yl)methyl)azetidine hydrochloride

Yield 72%; Melting Point 214° C.; $^1$H NMR (300 MHz, DMSO-d$_6$) δ 3.31-3.23 (m, 1H, C$\underline{H}$(CH$_2$)$_2$), 4.11-3.89 (m, 4H, CH(C$\underline{H_2}$)$_2$), 5.82-5.80 (d, J=6.9 Hz, 1H, CH), 7.94-7.03 (m, 11H, ArH), 9.26 (br(s), 2H, NH, HCl).

KHG26797
3-(naphthalene-2-yl(ortho-tolyloxy)methyl)azetidine hydrochloride

Yield 66%; Melting Point 213° C.; $^1$H NMR (300 MHz, DMSO-d$_6$) δ 2.35 (s, 3H, ArC$\underline{H_3}$), 3.43-3.37 (m, 1H, C$\underline{H}$(CH$_2$)$_2$), 4.16-3.91 (m, 4H, CH(C$\underline{H_2}$)$_2$), 5.85-5.83 (d, J=6.3 Hz, 1H, CH), 7.93-6.73 (m, 11H, ArH), 9.33 (br(s), 2H, NH, HCl).

KHG26798
3-(naphthalene-2-yl(meta-tolyloxy)methyl)azetidine hydrochloride

Yield 66%; Melting Point 210° C.; $^1$H NMR (300 MHz, DMSO-d$_6$) δ 2.19 (s, 3H, ArC$\underline{H_3}$), 3.28-3.22 (m, 1H, C$\underline{H}$(CH$_2$)$_2$), 4.07-3.87 (m, 4H, CH(C$\underline{H_2}$)$_2$), 5.84-5.82 (d, J=6.9 Hz, 1H, CH), 7.93-6.67 (m, 11H, ArH), 9.36 (br(s), 2H, NH, HCl).

KHG26799
3-(naphthalene-2-yl(para-tolyloxy)methyl)azetidine hydrochloride

Yield 78%; Melting Point 203° C.; $^1$H NMR (300 MHz, DMSO-d$_6$) δ 2.13 (s, 3H, ArC$\underline{H_3}$), 3.32-3.28 (m, 1H, C$\underline{H}$(CH$_2$)$_2$), 4.12-3.88 (m, 4H, CH(C$\underline{H_2}$)$_2$), 5.77-5.74 (d, J=6.9 Hz, 1H, CH), 7.91-6.87 (m, 11H, ArH), 9.18 (br(s), 2H, NH, HCl).

KHG26800
3-((2-chlorophenoxy)(naphthalene-2-yl)methyl)azetidine hydrochloride

Yield 81%; Melting Point 207° C.; $^1$H NMR (300 MHz, DMSO-d$_6$) δ 3.45-3.38 (m, 1H, C$\underline{H}$(CH$_2$)$_2$), 4.19-3.87 (m, 4H, CH(C$\underline{H_2}$)$_2$), 6.02-6.00 (d, J=7.2 Hz, 1H, CH), 7.95-6.87 (m, 11H, ArH), 9.29 (br(s), 2H, NH, HCl).

KHG26801
3-((3-chlorophenoxy)(naphthalene-2-yl)methyl)azetidine hydrochloride

Yield 41%; Melting Point 214° C.; $^1$H NMR (300 MHz, DMSO-d$_6$) δ 3.30-3.22 (m, 1H, C$\underline{H}$(CH$_2$)$_2$), 4.09-3.87 (m, 4H, CH(C$\underline{H_2}$)$_2$), 5.95-5.93 (d, J=6.3 Hz, 1H, CH), 7.95-6.93 (m, 11H, ArH), 9.47 and 9.35 (2br(s), 2H, NH, HCl).

KHG26802
3-((4-chlorophenoxy)(naphthalene-2-yl)methyl)azetidine hydrochloride

Yield 94%; Melting Point 211° C.; $^1$H NMR (300 MHz, DMSO-d$_6$) δ 3.29-3.22 (m, 1H, C$\underline{H}$(CH$_2$)$_2$), 4.09-3.89 (m, 4H, CH(C$\underline{H_2}$)$_2$), 5.85-5.83 (d, J=6.6 Hz, 1H, CH), 7.93-6.87 (m, 11H, ArH), 9.24 (br(s), 2H, NH, HCl).

KHG26803
3-(naphthalene-2-yl(2-(trifluoromethoxy)phenoxy)methyl)azetidine hydrochloride Yield 98%; Melting Point 228° C.; $^1$H NMR (300 MHz, DMSO-d$_6$) δ 3.62-3.54 (m, 1H, C$\underline{H}$(CH$_2$)$_2$), 4.04-3.84 (m, 4H, CH(C$\underline{H_2}$)$_2$), 6.10-6.08 (d, J=8.4 Hz, 1H, CH), 7.98-6.92 (m, 11H, ArH), 9.51 (br(s), 2H, NH, HCl).

KHG26804
3-(naphthalene-2-yl(3-(trifluoromethoxy)phenoxy)methyl)azetidine hydrochloride Yield 99%; Melting Point 217° C.; $^1$H NMR (300 MHz, DMSO-d$_6$) δ 3.39-3.27 (m, 1H, C$\underline{H}$(CH$_2$)$_2$), 4.14-3.90 (m, 4H, CH(C$\underline{H_2}$)$_2$), 5.99-5.97 (d, J=6.6 Hz, 1H, CH), 7.99-6.88 (m, 11H, ArH), 9.38 (br(s), 2H, NH, HCl).

KHG26805
3-(naphthalene-2-yl(4-(trifluoromethoxy)phenoxy)methyl)azetidine hydrochloride Yield 99%; Melting Point 209° C.; $^1$H NMR (300 MHz, DMSO-d$_6$) δ 3.27-3.20 (m, 1H, C$\underline{H}$(CH$_2$)$_2$), 4.08-3.88 (m, 4H, CH(C$\underline{H_2}$)$_2$), 5.88-5.86 (d, J=6.9 Hz, 1H, CH), 7.94-6.92 (m, 11H, ArH), 9.40 and 9.26 (2br(s), 2H, NH, HCl).

KHG26806
3-((3,4-difluorophenoxy)(naphthalene-2-yl)methyl)azetidine hydrochloride Yield 88%; Melting Point 212° C.; $^1$H NMR (300 MHz, DMSO-d$_6$) δ 3.37-3.31 (m, 1H, C$\underline{H}$(CH$_2$)$_2$), 4.09-3.89 (m, 4H, CH(C$\underline{H_2}$)$_2$), 5.91-5.89 (d, J=6.3 Hz, 1H, CH), 7.93-6.96 (m, 10H, ArH), 9.33 and 9.18 (2br(s), 2H, NH, HCl).

KHG26807
3-((3,4-dichlorophenoxy)(naphthalene-2-yl)methyl)azetidine hydrochloride Yield 55%; Melting Point 217° C.; $^1$H NMR (300 MHz, DMSO-d$_6$) δ 3.32-3.21 (m, 1H, C$\underline{H}$(CH$_2$)$_2$), 4.08-3.86 (m, 4H, CH(C$\underline{H_2}$)$_2$), 5.87-5.85 (d, J=6.9 Hz, 1H, CH), 7.93-6.79 (m, 10H, ArH), 9.39 and 9.20 (2br(s), 2H, NH, HCl).

KHG26808
3-((4-chloro-3-fluorophenyl)(ethoxy)methyl)azetidine hydrochloride

Yield 96%; Melting Point 215° C.; $^1$H NMR (300 MHz, DMSO-d$_6$) δ 1.18-1.13 (t, J=6.9 Hz, 3H, OCH$_2$C$\underline{H_3}$), 3.03-3.35 (m, 1H, C$\underline{H}$(CH$_2$)$_2$), 3.41-3.35 (q, J=6.9 Hz, 2H, OC$\underline{H_2}$CH$_3$), 3.90-3.69 (m, 4H, CH(C$\underline{H_2}$)$_2$), 4.72-4.70 (d, J=7.2 Hz, 1H, CH), 7.65-7.22 (m, 3H, ArH), 9.35 (br(s), 2H, NH, HCl).

KHG26809
3-((4-chloro-3-fluorophenyl)(phenoxy)methyl)azetidine hydrochloride

Yield 48%; Melting Point 201° C.; $^1$H NMR (300 MHz, DMSO-d$_6$) δ 3.29-3.21 (m, 1H, C$\underline{H}$(CH$_2$)$_2$), 4.03-3.86 (m, 4H, CH(C$\underline{H_2}$)$_2$), 5.73-5.71 (d, J=6.3 Hz, 1H, CH), 7.62-6.90 (m, 8H, ArH), 9.17 (br(s), 2H, NH, HCl).

KHG26810
3-((4-chloro-3-fluorophenyl)(2-fluorophenoxy)methyl)azetidine hydrochloride Yield 80%; Melting Point 198° C.; $^1$H NMR (300 MHz, DMSO-d$_6$) δ 3.34-3.26 (m, 1H, C$\underline{H}$(CH$_2$)$_2$), 4.04-3.85 (m, 4H, CH(C$\underline{H_2}$)$_2$), 5.88-5.85 (d, J=7.5 Hz, 1H, CH), 7.63-6.94 (m, 7H, ArH), 9.33 (br(s), 2H, NH, HCl).

KHG26811
3-((4-chloro-3-fluorophenyl)(3-fluorophenoxy)methyl)azetidine hydrochloride Yield 63%; Melting Point 217° C.; $^1$H NMR (300 MHz, DMSO-d$_6$) δ 3.30-3.17 (m, 1H, C$\underline{H}$(CH$_2$)$_2$), 4.02-3.80 (m, 4H, CH(C$\underline{H_2}$)$_2$), 5.84-5.82 (d, J=6.6 Hz, 1H, CH), 7.85-6.74 (m, 7H, ArH), 9.37 (br(s), 2H, NH, HCl).

KHG26812
3-((4-chloro-3-fluorophenyl)(4-fluorophenoxy)methyl)azetidine hydrochloride Yield 42%; Melting Point 218° C.; $^1$H NMR (300 MHz, DMSO-d$_6$) δ 3.31-3.21 (m, 1H, C$\underline{H}$(CH$_2$)$_2$), 4.08-3.82 (m, 4H, CH(C$\underline{H_2}$)$_2$), 5.76-5.74 (d, J=6.6 Hz, 1H, CH), 7.64-6.99 (m, 7H, ArH), 9.39 (br(s), 2H, NH, HCl).

KHG26813
3-((4-chloro-3-fluorophenyl)(ortho-tolyloxy)methyl)azetidine hydrochloride Yield 76%; Melting Point 205° C.; $^1$H NMR (300 MHz, DMSO-d$_6$) δ 2.31 (s, 3H, ArC$\underline{H_3}$), 3.33-3.26 (m, 1H, C$\underline{H}$(CH$_2$)$_2$), 4.08-3.89 (m, 4H, CH(C$\underline{H_2}$)$_2$), 5.77-5.75 (d, J=6.3 Hz, 1H, CH), 7.61-6.72 (m, 7H, ArH), 9.45 (br(s), 2H, NH, HCl).

KHG26814
3-((4-chloro-3-fluorophenyl)(meta-tolyloxy)methyl)azetidine hydrochloride Yield 97%; Melting Point 203° C. $^1$H NMR (300 MHz, DMSO-$d_6$) δ 2.21 (s, 3H, ArC$\underline{H}_3$), 3.26-3.21 (m, 1H, C$\underline{H}$(CH$_2$)$_2$), 3.98-3.87 (m, 4H, CH(C$\underline{H}_2$)$_2$), 5.74-5.72 (d, J=6.6 Hz, 1H, CH), 7.61-6.72 (m, 7H, ArH), 9.32 (br(s), 2H, NH, HCl).

KHG26815
3-((4-chloro-3-fluorophenyl)(para-tolyloxy)methyl)azetidine hydrochloride Yield 58%; Melting Point 173° C.; $^1$H NMR (300 MHz, DMSO-$d_6$) δ 2.17 (s, 3H, ArC$\underline{H}_3$), 3.26-3.19 (m, 1H, C$\underline{H}$(CH$_2$)$_2$), 3.99-3.86 (m, 4H, CH(C$\underline{H}_2$)$_2$), 5.68-5.66 (d, J=6.6 Hz, 1H, CH), 7.61-6.84 (m, 7H, ArH), 9.23 (br(s), 2H, NH, HCl).

KHG26816
3-((4-chloro-3-fluorophenyl)(2-chlorophenoxy)methyl)azetidine hydrochloride Yield 93%; Melting Point 220° C.; $^1$H NMR (300 MHz, DMSO-$d_6$) δ 3.36-3.28 (m, 1H, C$\underline{H}$(CH$_2$)$_2$), 4.03-3.86 (m, 4H, CH(C$\underline{H}_2$)$_2$), 5.98-5.96 (d, J=6.9 Hz, 1H, CH), 7.63-6.92 (m, 7H, ArH), 9.49 and 9.38 (2br(s), 2H, NH, HCl).

KHG26817
3-((4-chloro-3-fluorophenyl)(3-chlorophenoxy)methyl)azetidine hydrochloride Yield 32%; Melting Point 204° C.; $^1$H NMR (300 MHz, DMSO-$d_6$) δ 3.31-3.23 (m, 1H, C$\underline{H}$(CH$_2$)$_2$), 4.02-3.85 (m, 4H, CH(C$\underline{H}_2$)$_2$), 5.82-5.80 (d, J=5.7 Hz, 1H, CH), 7.60-6.91 (m, 7H, ArH), 9.31 (br(s), 2H, NH, HCl).

KHG26818
3-((4-chloro-3-fluorophenyl)(4-chlorophenoxy)methyl)azetidine hydrochloride Yield 94%; Melting Point 203° C.; $^1$H NMR (300 MHz, DMSO-$d_6$) δ 3.30-3.23 (m, 1H, C$\underline{H}$(CH$_2$)$_2$), 4.03-3.84 (m, 4H, CH(C$\underline{H}_2$)$_2$), 5.75-5.73 (d, J=6.3 Hz, 1H, CH), 7.63-6.98 (m, 7H, ArH), 9.22 (br(s), 2H, NH, HCl).

KHG26819
3-((4-chloro-3-fluorophenyl)(2-(trifluoromethoxy)phenoxy)methyl)azetidine hydrochloride Yield 96%; Melting Point 166° C.; $^1$H NMR (300 MHz, DMSO-$d_6$) δ 3.38-3.32 (m, 1H, C$\underline{H}$(CH$_2$)$_2$), 4.00-3.83 (m, 4H, CH(C$\underline{H}_2$)$_2$), 5.86-5.84 (d, J=7.8 Hz, 1H, CH), 7.66-7.00 (m, 7H, ArH), 9.04 (br(s), 2H, NH, HCl).

KHG26820
3-((4-chloro-3-fluorophenyl)(3-(trifluoromethoxy)phenoxy)methyl)azetidine hydrochloride Yield 91%; Melting Point 145° C.; $^1$H NMR (300 MHz, DMSO-$d_6$) δ 3.29-3.21 (m, 1H, C$\underline{H}$(CH$_2$)$_2$), 4.08-3.82 (m, 4H, CH(C$\underline{H}_2$)$_2$), 5.84-5.82 (d, J=6.6 Hz, 1H, CH), 7.63-6.91 (m, 7H, ArH), 9.27 (br(s), 2H, NH, HCl).

KHG26821
3-((4-chloro-3-fluorophenyl)(4-(trifluoromethoxy)phenoxy)methyl)azetidine hydrochloride Yield 90%; Melting Point 151° C.; $^1$H NMR (300 MHz, DMSO-$d_6$) δ 3.27-3.20 (m, 1H, C$\underline{H}$(CH$_2$)$_2$), 4.00-3.84 (m, 4H, CH(C$\underline{H}_2$)$_2$), 5.83-5.81 (d, J=6.6 Hz, 1H, CH), 7.62-7.06 (m, 7H, ArH), 9.48 and 9.42 (2br(s), 2H, NH, HCl).

KHG26822
3-((4-chloro-3-fluorophenyl)(3,4-difluorophenoxy)methyl)azetidine hydrochloride Yield 99%; Melting Point 216° C.; $^1$H NMR (300 MHz, DMSO-$d_6$) δ 3.30-3.18 (m, 1H, C$\underline{H}$(CH$_2$)$_2$), 4.03-3.86 (m, 4H, CH(C$\underline{H}_2$)$_2$), 5.78-5.76 (d, J=6.3 Hz, 1H, CH), 7.66-7.16 (m, 6H, ArH), 9.22 (br(s), 2H, NH, HCl).

KHG26823
3-((4-chloro-3-fluorophenyl)(3,4-dichlorophenoxy)methyl)azetidine hydrochloride Yield 98%; Melting Point 192° C.; $^1$H NMR (300 MHz, DMSO-$d_6$) δ 3.30-3.23 (m, 1H, C$\underline{H}$(CH$_2$)$_2$), 4.10-3.83 (m, 4H, CH(C$\underline{H}_2$)$_2$), 5.85-5.83 (d, J=6.0 Hz, 1H, CH), 7.66-6.98 (m, 6H, ArH), 9.26 (br(s), 2H, NH, HCl).

KHG26878
3-((benzyloxy)(4-chloro-3-fluorophenyl)methyl)azetidine hydrochloride

Yield 82%; Melting Point 191° C.; $^1$H NMR (300 MHz, DMSO-$d_6$) δ 3.10-3.02 (m, 1H, C$\underline{H}$(CH$_2$)$_2$), 3.90-3.74 (m, 4H, CH(C$\underline{H}_2$)$_2$), 4.44-4.32 (dd, 2H, J=11.7 Hz, OC$\underline{H}_2$Ar), 4.75-4.73 (d, J=6.9 Hz, 1H, CH), 7.66-7.24 (m, 8H, ArH), 9.30 and 9.13 (2br(s), 2H, NH, HCl).

KHG26879
azetidine-3-ly(4-chloro-3-fluorophenyl)methyl benzoate hydrochloride

Yield 82%; Melting Point 207° C.; $^1$H NMR (300 MHz, DMSO-$d_6$) δ 3.48-3.33 (m, 1H, C$\underline{H}$(CH$_2$)$_2$), 4.12-3.86 (m, 4H, CH(C$\underline{H}_2$)$_2$), 6.17-6.15 (d, J=6.9 Hz, 1H, CH), 8.14-7.31 (m, 8H, ArH), 9.18 (br(s), 2H, NH, HCl).

KHG26890
3-((3-chloro-4-fluorophenyl)(phenoxy)methyl)azetidine hydrochloride

Yield 30%; Melting Point 208° C.; $^1$H NMR (300 MHz, DMSO-$d_6$) δ 3.28-3.28 (m, 1H, C$\underline{H}$(CH$_2$)$_2$), 4.01-3.83 (m, 4H, CH(C$\underline{H}_2$)$_2$), 5.77-5.75 (d, J=6.9 Hz, 1H, CH), 7.66-6.89 (m, 8H, ArH), 9.29 (br(s), 2H, NH, HCl).

KHG26891
3-((3-chloro-4-fluorophenyl)(2-fluorophenoxy)methyl)azetidine hydrochloride Yield 99%; Melting Point 194° C.; $^1$H NMR (300 MHz, DMSO-$d_6$) δ 3.36-3.25 (m, 1H, C$\underline{H}$(CH$_2$)$_2$), 4.03-3.85 (m, 4H, CH(C$\underline{H}_2$)$_2$), 5.90-5.88 (d, J=7.8 Hz, 1H, CH), 7.67-6.92 (m, 7H, ArH), 9.38 (br(s), 2H, NH, HCl).

KHG26892
3-((3-chloro-4-fluorophenyl)(3-fluorophenoxy)methyl)azetidine hydrochloride Yield 99%; Melting Point 209° C.; $^1$H NMR (300 MHz, DMSO-$d_6$) δ 3.33-3.18 (m, 1H, C$\underline{H}$(CH$_2$)$_2$), 4.01-3.78 (m, 4H, CH(C$\underline{H}_2$)$_2$), 5.83-5.80 (d, J=6.9 Hz, 1H, CH), 7.67-6.73 (m, 7H, ArH), 9.30 (br(s), 2H, NH, HCl).

KHG26893
3-((3-chloro-4-fluorophenyl)(4-fluorophenoxy)methyl)azetidine hydrochloride Yield 74%; Melting Point 211° C.; $^1$H NMR (300 MHz, DMSO-$d_6$) δ 3.27-3.19 (m, 1H, C$\underline{H}$(CH$_2$)$_2$), 4.00-3.78 (m, 4H, CH(C$\underline{H}_2$)$_2$), 5.72-5.70 (d, J=6.3 Hz, 1H, CH), 7.65-6.97 (m, 7H, ArH), 9.31 (br(s), 2H, NH, HCl).

KHG26894
3-((3-chloro-4-fluorophenyl)(2-chlorophenoxy)methyl)azetidine hydrochloride Yield 96%; Melting Point 188° C.; $^1$H NMR (300 MHz, DMSO-$d_6$) δ 3.38-3.29 (m, 1H, C$\underline{H}$(CH$_2$)$_2$), 4.05-3.85 (m, 4H, CH(C$\underline{H}_2$)$_2$), 5.97-5.95 (d, J=7.2 Hz, 1H, CH), 7.67-6.92 (m, 7H, ArH), 9.41 and 9.34 (2br(s), 2H, NH, HCl).

KHG26895
3-((3-chloro-4-fluorophenyl)(3-chlorophenoxy)methyl)azetidine hydrochloride Yield 99%; Melting Point 205° C.; $^1$H NMR (300 MHz, DMSO-$d_6$) δ 3.27-3.19 (m, 1H, C$\underline{H}$(CH$_2$)$_2$), 4.05-3.78 (m, 4H, CH(C$\underline{H}_2$)$_2$), 5.86-5.84 (d, J=6.6 Hz, 1H, CH), 7.67-6.92 (m, 7H, ArH), 9.39 (br(s), 2H, NH, HCl).

KHG26896
3-((3-chloro-4-fluorophenyl)(4-chlorophenoxy)methyl)azetidine hydrochloride

KHG26897

3-((3-chloro-4-fluorophenyl)(ortho-tolyloxy)methyl)azetidine hydrochloride

Yield 78%; Melting Point 209° C.; $^1$H NMR (300 MHz, DMSO-$d_6$) δ 2.30 (s, 3H, ArCH$_3$), 3.35-3.27 (m, 1H, CH(CH$_2$)$_2$), 4.08-3.87 (m, 4H, CH(CH$_2$)$_2$), 5.73-5.71 (d, J=6.3 Hz, 1H, CH), 7.65-6.73 (m, 7H, ArH), 9.28 and 9.18 (2br(s), 2H, NH, HCl).

KHG26898

3-((3-chloro-4-fluorophenyl)(meta-tolyloxy)methyl)azetidine hydrochloride

Yield 91%; Melting Point 151° C.; $^1$H NMR (300 MHz, DMSO-$d_6$) δ 2.22 (s, 3H, ArCH$_3$), 3.26-3.19 (m, 1H, CH(CH$_2$)$_2$), 3.99-3.78 (m, 4H, CH(CH$_2$)$_2$), 5.75-5.73 (d, J=6.6 Hz, 1H, CH), 7.65-6.72 (m, 7H, ArH), 9.34 (br(s), 2H, NH, HCl).

KHG26899

3-((3-chloro-4-fluorophenyl)(para-tolyloxy)methyl)azetidine hydrochloride

Yield 43%; Melting Point 183° C.; $^1$H NMR (300 MHz, DMSO-$d_6$) δ 2.17 (s, 3H, ArCH$_3$), 3.26-3.19 (m, 1H, CH(CH$_2$)$_2$), 4.04-3.78 (m, 4H, CH(CH$_2$)$_2$), 5.70-5.67 (d, J=6.9 Hz, 1H, CH), 7.63-6.84 (m, 7H, ArH), 9.26 (br(s), 2H, NH, HCl).

KHG26900

3-((3-chloro-4-fluorophenyl)(2-(trifluoromethoxy)phenoxy)methyl)azetidine hydrochloride Yield 99%; Melting Point 157° C.; $^1$H NMR (300 MHz, DMSO-$d_6$) δ 3.38-3.30 (m, 1H, CH(CH$_2$)$_2$), 4.05-3.78 (m, 4H, CH(CH$_2$)$_2$), 5.91-5.88 (d, J=7.8 Hz, 1H, CH), 7.66-7.00 (m, 7H, ArH), 9.14 (br(s), 2H, NH, HCl).

KHG26901

3-((3-chloro-4-fluorophenyl)(3-(trifluoromethoxy)phenoxy)methyl)azetidine hydrochloride Yield 99%; Melting Point 157° C.; $^1$H NMR (300 MHz, DMSO-$d_6$) δ 3.29-3.22 (m, 1H, CH(CH$_2$)$_2$), 4.03-3.79 (m, 4H, CH(CH$_2$)$_2$), 5.88-5.86 (d, J=6.3 Hz, 1H, CH), 7.69-6.90 (m, 7H, ArH), 9.39 (br(s), 2H, NH, HCl).

KHG26902

3-((3-chloro-4-fluorophenyl)(3,4-difluorophenoxy)methyl)azetidine hydrochloride

Yield 31%; Melting Point 187° C.; $^1$H NMR (300 MHz, DMSO-$d_6$) δ 3.30-3.22 (m, 1H, CH(CH$_2$)$_2$), 3.99-3.79 (m, 4H, CH(CH$_2$)$_2$), 5.80-5.78 (d, J=6.6 Hz, 1H, CH), 7.65-6.79 (m, 7H, ArH), 9.47 and 9.35 (2br(s), 2H, NH, HCl).

KHG26903

3-((3-chloro-4-fluorophenyl)(3,4-dichlorophenoxy)methyl)azetidine hydrochloride

Yield 83%; melting point 186° C.; $^1$H NMR (300 MHz, DMSO-$d_6$) δ 3.28-3.21 (m, 1H, CH(CH$_2$)$_2$), 4.00-3.82 (m, 4H, CH(CH$_2$)$_2$), 5.83-5.81 (d, J=6.0 Hz, 1H, CH), 7.68-6.96 (m, 7H, ArH), 9.26 (br(s), 2H, NH, HCl).

KHG27270

3-((3,4-difluorophenyl)(propoxy)methyl)azetidine hydrochloride

Yield 67%; Melting Point 116° C.; $^1$H NMR (600 MHz, DMSO-$d_6$) δ 0.82 (t, 3H, CH$_3$), 1.48 (m, 2H, CH$_2$), 2.94 (m, 1H, CH), 3.20 (t, 2H, CH$_2$) 3.65-3.84 (m, 4H, CH(CH$_2$)$_2$), 4.57 (dd, 1H, J=7.2 Hz, OCH), 7.15-7.42 (m, 3H, ArH), 9.16 (2br(s), 2H, NH, HCl).

KHG27271

3-((3,4-difluorophenyl)(2-fluorophenoxy)methyl)azetidine hydrochloride

Yield 46%; Melting Point 187° C.; $^1$H NMR (600 MHz, DMSO-$d_6$) δ 3.23-3.29 (m, 1H, J=7.8 Hz, CH), 3.76-4.00 (m, 4H, CH(CH$_2$)$_2$), 5.78-5.80 (d, 1H, J=7.8 Hz, OCH), 6.91-7.50 (m, 7H, ArH), 9.25 (2br(s), 2H, NH, HCl).

KHG27273

3-((3,4-difluorophenyl)(4-fluorophenoxy)methyl)azetidine hydrochloride

Yield 38%; Melting Point 188° C.; $^1$H NMR (600 MHz, DMSO-$d_6$) δ 3.32 (m, 1H, CH), 3.77-3.98 (m, 4H, CH(CH$_2$)$_2$), 5.68-5.69 (d, 1H, J=7.2 Hz CH), 6.96-7.46 (m, 7H, ArH), 9.20 (2br(s), 2H, NH, HCl).

KHG27274

3-((2-chlorophenoxy)(3,4-difluorophenyl)methyl)azetidine hydrochloride

Yield 54%; Melting Point 174° C.; $^1$H NMR (600 MHz, DMSO-$d_6$) δ 3.26-3.30 3.32 (m, 1H, CH), 3.81-4.01 (m, 4H, CH(CH$_2$)$_2$), 5.90-5.91 (d, 1H, J=7.2 Hz, CH), 6.89-7.48 (m, 7H, ArH), 9.32-9.42 (2br(s), 2H, NH, HCl).

KHG27275

3-((3-chlorophenoxy)(3,4-difluorophenyl)methyl)azetidine hydrochloride

Yield 23%; Melting Point 152° C.; $^1$H NMR (600 MHz, DMSO-$d_6$) δ 3.16-3.20 (m, 1H, CH), 3.76-4.00 (m, 4H, CH(CH$_2$)$_2$), 5.78-5.79 (d, 1H, J=6.6 Hz, CH), 6.89-7.49 (m, 7H, ArH), 9.34 (2br(s), 2H, NH, HCl).

KHG27276

3-((3,4-difluorophenyl)(ortho-tolyloxy)methyl)azetidine hydrochloride

Yield 74%; Melting Point 151° C.; $^1$H NMR (600 MHz, DMSO-$d_6$) δ 2.26 (s, 3H, CH$_3$) 3.25-3.29 (m, 1H, CH), 3.80-4.06 (m, 4H, CH(CH$_2$)$_2$), 5.67-5.68 (d, 1H, J=6.6 Hz, CH), 6.70-7.46 (m, 7H, ArH), 9.23 (2br(s), 2H, NH, HCl).

KHG27277

3-((3,4-difluorophenyl)(meta-tolyloxy)methyl)azetidine hydrochloride

Yield 50%; Melting Point 189° C.; $^1$H NMR (600 MHz, DMSO-$d_6$) δ 2.17 (s, 3H, CH$_3$), 3.15-3.19 (m, 1H, CH), 3.76-3.95 (m, 4H, CH(CH$_2$)$_2$), 5.69-5.71 (d, 1H, J=7.2 Hz, CH), 6.68-7.47 (m, 7H, ArH), 9.37 (2br(s), 2H, NH, HCl).

KHG27278

3-((3,4-difluorophenyl)(para-tolyloxy)methyl)azetidine hydrochloride

Yield 46%; Melting Point 159° C.; $^1$H NMR (600 MHz, DMSO-$d_6$) δ 2.13 (s, 3H, CH$_3$), 3.15-3.19 (m, 1H, CH), 3.76-3.98 (m, 4H, CH(CH$_2$)$_2$), 5.65-5.66 (d, 1H, J=6.6 Hz, CH), 6.60-7.46 (m, 7H, ArH), 9.32 (2br(s), 2H, NH, HCl).

KHG27284

3-(1-(naphthalene-2-yloxy)butyl)azetidine hydrochloride

Yield 70%; Melting Point 77° C.; $^1$H NMR (600 MHz, DMSO-$d_6$) δ 0.83 (t, 3H, (CH$_2$)CH$_3$), 1.28-1.34 (m, 2H, CH$_2$), 1.51-2.47 (m, 2H, CH$_2$), 3.14-3.28 (m, 1H, CH), 3.76-3.98 (m, 4H, CH(CH$_2$)$_2$), 4.75-4.77 (t, 1H, J=5.4 Hz, CH), 7.26-7.84 (m, 7H, ArH), 9.09 (2br(s), 2H, NH, HCl).

KHG27285

3-((naphthalene-2-yloxy)(phenyl)methyl)azetidine hydrochloride

Yield 60%; Melting Point 183° C.; $^1$H NMR (600 MHz, DMSO-$d_6$) δ 3.24-3.30 (m, 1H, CH), 4.10-4.30 (m, 4H, CH(C$\underline{H_2}$)$_2$), 5.49 (s, 1H, CH), 7.02-7.72 (m, 7H, ArH), 9.85 (2br(s), 2H, NH, HCl).

Example 9

Synthesis of tertiary butyl 3-((3,4-dichlorophenyl)(hydroxy)methyl)azetidine-1-carboxylate

[Reaction Scheme 2a]

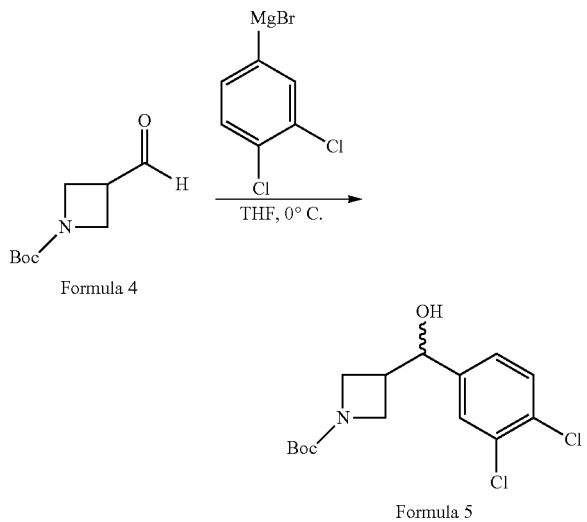

Formula 4

Formula 5

Tertiary butyl 3-formyl azetidine-1-carboxylate (1.3 g, 7.0 mmol) was slowly added to (3,4-dichlorophenyl)magnesium bromide (22 mL, 21 mmol) dissolved in the distilled tetrahydrofuran solution at 0° C., and the mixture was stirred at the same temperature for 3 hours. Thereafter, saturated ammonium chloride aqueous solution (15 mL) was slowly added at 0° C., and the mixture was stirred at room temperature for 1 hour. The reaction mixture was extracted with methylene chloride (30 mL) three times, and the organic layer was washed with saturated sodium chloride solution and distilled water once, respectively and dried over anhydrous magnesium sulfate. The solvent was removed by reduced pressure evaporation to obtain a yellow liquid, which was purified by flash chromatography (n-hexane:ethyl acetate (4:1, v/v)). The product was identified as a single compound by TLC (n-hexane:ethyl acetate (4:1, v/v)).

Yield: 68%; $^1$H NMR (300 MHz, CDCl$_3$) δ 1.45 (s, 9H, CO$_2$C(C$\underline{H_3}$)$_3$), 2.74-2.86 (m, 1H, C$\underline{H}$(CH$_2$)$_2$), 2.95-2.96 (d, 1H, J=3.9 Hz, OH), 3.67-4.01 (m, 4H, CH(C$\underline{H_2}$)$_2$), 4.76-4.79 (dd, 1H, J=3.6 Hz, CH), 7.18-7.48 (m, 3H, ArH).

Example 10

Synthesis of tertiary butyl 3-(1-(3,4-dichlorophenyl)-2-(methylsulfonyl)ethyl)azetidine-1-carboxylate

[Reaction Scheme 2b]

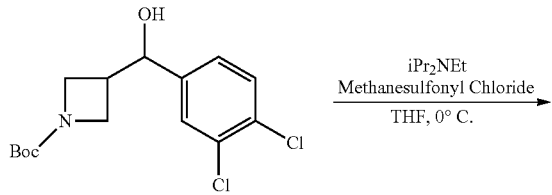

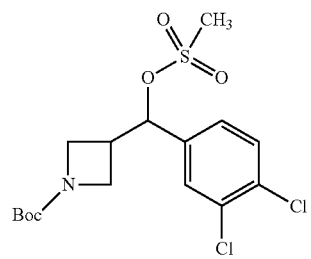

Methanesulfonyl chloride (0.69 mL, 6.0 mmol) was added to tertiary butyl 3-(1-(3,4-dichlorophenyl)-2-(methylsulfonyl)ethyl)azetidine-1-carboxylate (1.0 g, 3.0 mmol) and diisopropylethylamine (1.7 mL, 10 mmol) dissolved in the distilled tetrahydrofuran solution (15 mL), and the mixture was stirred at 0° C. for 10 hours. The reaction mixture was subjected to reduced pressure evaporation and dissolved in methylene chloride (90 mL). Then, the resultant was washed with a saturated sodium bicarbonate aqueous solution and distilled water once, respectively and dried over anhydrous magnesium sulfate to remove the solvent. Finally, a yellow liquid was obtained, and purified by flash chromatography (n-hexane:ethyl acetate (2:1, v/v)). The product was identified as a single compound by TLC (n-hexane:ethyl acetate (2:1, v/v)).

Yield: 57%; $^1$H NMR (300 MHz, CDCl$_3$) δ 1.424 (s, 9H, CO$_2$C(C$\underline{H_3}$)$_3$), 2.83 (s, 3H, SO$_2$C$\underline{H_3}$), 2.95-3.07 (m, 1H, CH), 3.54-4.22 (m, 4H, CH(C$\underline{H_2}$)$_2$), 5.61 (d, 1H, J=9.0 Hz, OCH), 7.23-7.50 (m, 3H, ArH).

Example 11

Synthesis of tertiary butyl 3-((3,4-dichlorophenyl)(2H-tetrazol-2-yl)methyl)azetidine-1-carboxylate

[Reaction Scheme 2c]

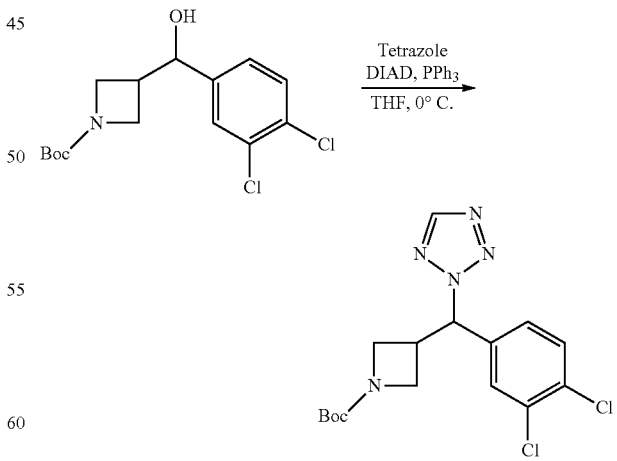

Tetrazole (90.0 mg, 1.28 mmol) was added to tertiary butyl 3-((3,4-dichlorophenyl)(hydroxy)methyl)azetidine-1-carboxylate (200 mg, 0.638 mmol) and triphenylphosphine (335 mg, 1.28 mmol) dissolved in the distilled tetrahydrofuran solution (15.0 mL), and diisopropyl azocarboxylate (0.25 mL, 1.28 mmol) was slowly added thereto at 0° C., and the mixture was stirred at room temperature for one day. The solvent of the reaction mixture was removed by reduced pressure evaporation to obtain a yellow liquid, which was purified by flash chromatography (n-hexane:ethyl acetate (4:1, v/v)). The product was identified as a single compound by TLC (n-hexane:ethyl acetate (4:1, v/v)) (yield: 88%, white solid). This white solid was dissolved in 10 mL of methanol solution, and 1 N HCl (3.0 mL) was added thereto, and heated to reflux at 60° C. for one day. Thereafter, the solvent of the reaction mixture was removed by reduced pressure evaporation to obtain the title compound (KHG27280).

Example 12

Synthesis of tertiary butyl 3-((cyclopentyloxy)(3,4-dichlorophenyl)methyl)azetidine-1-carboxylate

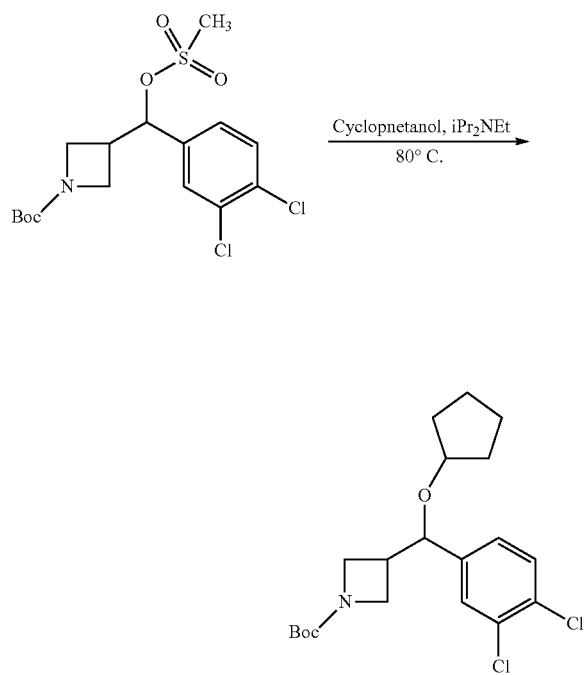

Tertiary butyl 3-(1-(3,4-dichlorophenyl)-2-(methylsulfonyl)ethyl)azetidine-1-carboxylate (0.2 g, 0.49 mmol) and cyclopentanol (3.0 mL, 2.4 mmol) were stirred at 80° C. for one day. The reaction mixture was dissolved in methylene chloride (70 mL), and the organic layer was washed with saturated sodium carbonate ($Na_2CO_3$) and distilled water once, respectively, and dried over anhydrous magnesium sulfate to remove the solvent. Finally, a colorless liquid was obtained, and purified by flash chromatography (n-hexane:ethyl acetate (2:1, v/v)). The product was identified as a single compound by TLC (n-hexane:ethyl acetate (2:1, v/v)).

Yield: 73%; $^1$H NMR (300 MHz, DMSO-$d_6$) δ 1.44 (s, 9H, $CO_2C(\underline{CH_3})_3$), 1.23-1.71 (m, 8H, PenH), 2.60-2.72 (m, 1H, CH), 3.55-3.60 (m, 1H, OCH), 3.72-3.96 (m, 4H, CH($\underline{CH_2})_2$), 4.31 (d, 1H, J=8.1 Hz, CH), 7.14-7.43 (m, 3H, ArH)

Example 13

Synthesis of 3-((cyclopentyloxy)(3,4-dichlorophenyl)methyl)azetidine hydrochloride (KHG 27254)

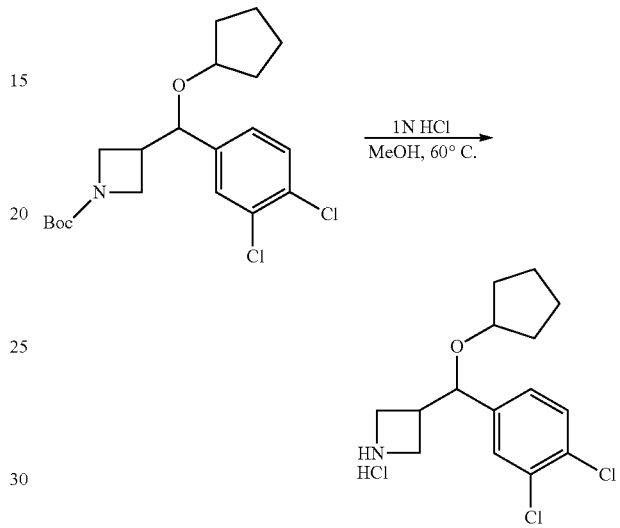

1 N HCl (3.0 mL) was added to 10 mL of tertiary butyl 3-(1-(3,4-dichlorophenyl)-2-(methylsulfonyl)ethyl)azetidine-1-carboxylate (0.15 g, 0.36 mmol) dissolved in the methanol solution and heated to reflux at 60° C. for one day. Thereafter, the solvent of the reaction mixture was removed by reduced pressure evaporation to obtain the title compound.

Yield 97%; Melting Point 174.6° C.; $^1$H NMR (300 MHz, DMSO-$d_6$) δ 1.25-1.88 (m, 8H, cyclopentyl-H), 2.91-2.98 (m, 1H, CH), 3.68-3.98 (m, 4H, CH($\underline{CH_2})_2$), 4.76 (d, 1H, J=7.5 Hz, CH), 7.19-7.83 (m, 3H, ArH), 9.27 (2br(s), 2H, NH, HCl).

The following compounds were synthesized according to the same method

KHG27252

3-(tertiarybutoxy(3,4-dichlorophenyl)methyl)azetidine hydrochloride

Yield 72%; Melting Point 159.9° C.; $^1$H NMR (300 MHz, DMSO-$d_6$) δ 1.12 (s, 9H, tert-Butyl-H), 2.84-2.86 (m, 1H, CH), 3.03-3.06 (m, 1H, OCH), 3.78-3.87 (m, 4H, CH($\underline{CH_2})_2$), 4.60-4.63 (d, 1H, J=7.2 Hz, CH), 7.20-7.66 (m, 3H, ArH), 9.13 (2br(s), 2H, NH, HCl).

KHG27253

3-(cyclobutoxy(3,4-dichlorophenyl)methyl)azetidine hydrochloride

Yield 68%; Melting Point 166.1° C.; $^1$H NMR (300 MHz, DMSO-$d_6$) δ 1.15-2.14 (m, 6H, cyclobutyl-H), 2.92-3.05 (m, 1H, CH), 3.67-3.69 (m, 1H, OCH), 3.78-3.87 (m, 4H, CH($\underline{CH_2})_2$), 4.60-4.63 (d, 1H, J=7.2 Hz, CH), 7.20-7.66 (m, 3H, ArH), 9.13 (2br(s), 2H, NH, HCl).

KHG27255

3-((cyclohexyloxy)(3,4-dichlorophenyl)methyl)azetidine hydrochloride

Yield 64%; Melting Point 189.4° C.; $^1$H NMR (300 MHz, DMSO-$d_6$) δ 1.18-2.01 (m, 10H, cyclohexyl-H), 2.91-2.98

(m, 1H, CH), 3.16-3.22 (m, 1H, OCH), 3.72-3.90 (m, 4H, CH(CH$_2$)$_2$), 4.87 (d, 1H, J=7.2 Hz, CH), 7.36-7.69 (m, 3H, ArH), 9.17 (2br(s), 2H, NH, HCl).

KHG27279

2-(azetidine-3-ly(naphthanlene-2-yl)methyl)-2H-tetrazole hydrochloride

Yield 65%; Melting Point 215.3° C.; $^1$H NMR (600 MHz, DMSO-d$_6$) δ 3.81-4.12 (m, 4H, CH(CH$_2$)$_2$), 6.82 (d, 1H, J=10.2 Hz, CH), 7.40-8.00 (m, 7H, ArH), 9.04 (s, 1H, TZCH), 9.22-9.14 (2br(s), 2H, NH, HCl).

KHG27280

2-(azetidine-3-ly(3,4-dichlorophenyl)methyl)-2H-tetrazole hydrochloride

Yield 54%; Melting Point 185.4° C.; $^1$H NMR (600 MHz, DMSO-d$_6$) δ 3.76-4.06 (m, 4H, CH(CH$_2$)$_2$), 6.82 (d, 1H, J=9.6 Hz, CH), 7.40-7.73 (m, 3H, ArH), 9.05 (s, 1H, TZCH), 9.45 (2br(s), 2H, NH, HCl).

KHG27281

2-(azetidine-3-ly(3-chloro-4-fluorophenyl)methyl)-2H-tetrazole hydrochloride

Yield 62%; Melting Point 174.1° C.; $^1$H NMR (600 MHz, DMSO-d$_6$) δ 3.32-4.07 (m, 4H, CH(CH$_2$)$_2$), 6.80-6.81 (d, 1H, J=10.2 Hz, CH), 7.46-7.71 (m, 3H, ArH), 9.04 (s, 1H, TZCH), 9.43 (2br(s), 2H, NH, HCl).

KHG27282

2-(azetidine-3-ly(3,4-difluorophenyl)methyl)-2H-tetrazole hydrochloride

Yield 74%; Melting Point 173.3° C.; $^1$H NMR (600 MHz, DMSO-d$_6$) δ 3.73-4.07 (m, 4H, CH(CH$_2$)$_2$), 6.80 (d, 1H, J=10.2 Hz, CH), 7.29-7.57 (m, 3H, ArH), 9.04 (s, 1H, TZCH), 9.46 (2br(s), 2H, NH, HCl).

Example 14

Synthesis of 1-methyl-3-(naphthalene-2-yl(phenoxy)methyl)azetidine (KHG26907)

[Reaction Scheme 3]

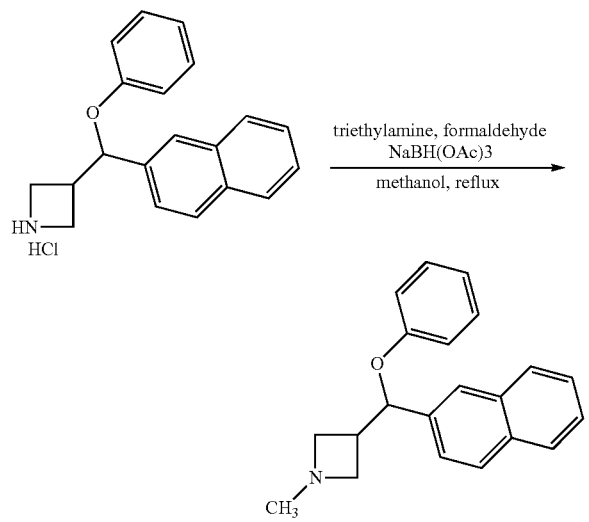

Triethylamine (0.2 mL, 1.4 mmol) was added to 3-(naphthalen-2-yl(phenoxy)methyl)azetidine hydrochloride (0.3 g, 0.92 mmol) dissolved in the methanol solution (20 mL), and stirred at room temperature for 1 hour. Formaldehyde (37% aqueous solution, 0.32 mL, 3.7 mmol), acetic acid (0.21 mL, 3.7 mmol) and sodium acetate borohydride (0.78 g, 3.7 mmol) were added in this order to the reaction mixture, and heated to reflux for one day. The temperature was reduced to room temperature, and 1N caustic soda solution (10 mL) was added thereto, followed by stirring for 30 minutes. The reaction mixture was extracted with methylene chloride, and the organic layer was washed with distilled water once, and then dried over anhydrous magnesium sulfate. The solvent was removed by reduced pressure evaporation to obtain a light yellow oily liquid, which was purified by flash chromatography (methylene chloride:methanol=9:1) to obtain a light yellow oily liquid (0.17 g).

Yield: 61%, light yellow liquid; $^1$H NMR (300 MHz, CDCl$_3$) δ 2.47 (s, 3H, NCH$_3$), 3.12 (m, 1H, CH), 3.29-3.60 (m, 4H, azetidine H), 5.49 (d, 1H, J=7.8 Hz, CH), 6.88-7.87 (m, 12H, ArH).

The synthesized compounds are summarized in the following Table 1.

TABLE 1

| Compound No. | R$_1$ | R$_2$ | R$_3$ | X |
|---|---|---|---|---|
| KHG26749 | H | H | C$_6$H$_5$ | HCl |
| KHG26750 | H | CH$_3$ | C$_6$H$_5$ | HCl |
| KHG26751 | H | CH$_2$CH$_3$ | C$_6$H$_5$ | HCl |
| KHG26752 | H | H | C$_6$H$_4$(4-Cl) | HCl |
| KHG26753 | H | CH$_3$ | C$_6$H$_4$(4-Cl) | HCl |
| KHG26754 | H | CH$_2$CH$_3$ | C$_6$H$_4$(4-Cl) | HCl |
| KHG26755 | H | H | C$_6$H$_3$(3,4-di Cl) | HCl |
| KHG26756 | H | CH$_3$ | C$_6$H$_3$(3,4-di Cl) | HCl |
| KHG26757 | H | CH$_2$CH$_3$ | C$_6$H$_3$(3,4-di Cl) | HCl |
| KHG26758 | H | H | CH$_2$C$_6$H$_5$ | HCl |
| KHG26759 | H | CH$_3$ | C$_6$H$_4$(2-Me) | HCl |
| KHG26765 | H | C$_6$H$_5$ | C$_6$H$_5$ | HCl |
| KHG26766 | H | C$_6$H$_5$ | C$_6$H$_4$(4-Cl) | HCl |
| KHG26767 | H | C$_6$H$_5$ | C$_6$H$_3$(3,4-di Cl) | HCl |
| KHG26768 | H | CH$_2$C$_6$H$_5$ | C$_6$H$_5$ | HCl |
| KHG26769 | H | CH$_2$C$_6$H$_5$ | C$_6$H$_4$(4-Cl) | HCl |
| KHG26770 | H | CH$_2$C$_6$H$_5$ | C$_6$H$_3$(3,4-di Cl) | HCl |
| KHG26771 | H | COC$_6$H$_5$ | C$_6$H$_5$ | HCl |
| KHG26772 | H | COC$_6$H$_5$ | C$_6$H$_4$(4-Cl) | HCl |
| KHG26773 | H | COC$_6$H$_5$ | C$_6$H$_3$(3,4-di Cl) | HCl |
| KHG26774 | H | C$_6$H$_4$(2-CH$_3$) | C$_6$H$_3$(3,4-di Cl) | HCl |
| KHG26775 | H | C$_6$H$_4$(3-CH$_3$) | C$_6$H$_3$(3,4-di Cl) | HCl |
| KHG26776 | H | C$_6$H$_4$(4-CH$_3$) | C$_6$H$_3$(3,4-di Cl) | HCl |
| KHG26779 | H | CH$_2$CH$_2$CH$_3$ | C$_6$H$_3$(3,4-di Cl) | HCl |
| KHG26780 | H | C$_6$H$_4$(2-F) | C$_6$H$_3$(3,4-di Cl) | HCl |
| KHG26781 | H | C$_6$H$_4$(3-F) | C$_6$H$_3$(3,4-di Cl) | HCl |
| KHG26782 | H | C$_6$H$_4$(4-F) | C$_6$H$_3$(3,4-di Cl) | HCl |
| KHG26783 | H | C$_6$H$_4$(2-Cl) | C$_6$H$_3$(3,4-di Cl) | HCl |
| KHG26784 | H | C$_6$H$_4$(3-Cl) | C$_6$H$_3$(3,4-di Cl) | HCl |
| KHG26785 | H | C$_6$H$_4$(4-Cl) | C$_6$H$_3$(3,4-di Cl) | HCl |
| KHG26786 | H | C$_6$H$_4$(2-OCF$_3$) | C$_6$H$_3$(3,4-di Cl) | HCl |
| KHG26787 | H | C$_6$H$_4$(3-OCF$_3$) | C$_6$H$_3$(3,4-di Cl) | HCl |
| KHG26788 | H | C$_6$H$_4$(4-OCF$_3$) | C$_6$H$_3$(3,4-di Cl) | HCl |
| KHG26789 | H | C$_6$H$_3$(3,4-di F) | C$_6$H$_3$(3,4-di Cl) | HCl |
| KHG26790 | H | C$_6$H$_3$(3,4-di Cl) | C$_6$H$_3$(3,4-di Cl) | HCl |
| KHG26791 | H | CH$_2$CH$_3$ | C$_{10}$H$_7$ | HCl |
| KHG26792 | H | CH$_2$CH$_2$CH$_3$ | C$_{10}$H$_7$ | HCl |
| KHG26793 | H | C$_6$H$_5$ | C$_{10}$H$_7$ | HCl |
| KHG26794 | H | C$_6$H$_4$(2-F) | C$_{10}$H$_7$ | HCl |
| KHG26795 | H | C$_6$H$_4$(3-F) | C$_{10}$H$_7$ | HCl |
| KHG26796 | H | C$_6$H$_4$(4-F) | C$_{10}$H$_7$ | HCl |
| KHG26797 | H | C$_6$H$_4$(2-CH$_3$) | C$_{10}$H$_7$ | HCl |
| KHG26798 | H | C$_6$H$_4$(3-CH$_3$) | C$_{10}$H$_7$ | HCl |
| KHG26799 | H | C$_6$H$_4$(4-CH$_3$) | C$_{10}$H$_7$ | HCl |
| KHG26800 | H | C$_6$H$_4$(2-Cl) | C$_{10}$H$_7$ | HCl |
| KHG26801 | H | C$_6$H$_4$(3-Cl) | C$_{10}$H$_7$ | HCl |
| KHG26802 | H | C$_6$H$_4$(4-Cl) | C$_{10}$H$_7$ | HCl |
| KHG26803 | H | C$_6$H$_4$(2-OCF$_3$) | C$_{10}$H$_7$ | HCl |
| KHG26804 | H | C$_6$H$_4$(3-OCF$_3$) | C$_{10}$H$_7$ | HCl |
| KHG26805 | H | C$_6$H$_4$(4-OCF$_3$) | C$_{10}$H$_7$ | HCl |
| KHG26806 | H | C$_6$H$_3$(3,4-di F) | C$_{10}$H$_7$ | HCl |
| KHG26807 | H | C$_6$H$_3$(3,4-di Cl) | C$_{10}$H$_7$ | HCl |
| KHG26808 | H | CH$_2$CH$_3$ | C$_6$H$_3$(3-F,4-Cl) | HCl |
| KHG26809 | H | C$_6$H$_5$ | C$_6$H$_3$(3-F,4-Cl) | HCl |

TABLE 1-continued

| Compound No. | $R_1$ | $R_2$ | $R_3$ | X |
|---|---|---|---|---|
| KHG26810 | H | $C_6H_4$(2-F) | $C_6H_3$(3-F,4-Cl) | HCl |
| KHG26811 | H | $C_6H_4$(3-F) | $C_6H_3$(3-F,4-Cl) | HCl |
| KHG26812 | H | $C_6H_4$(4-F) | $C_6H_3$(3-F,4-Cl) | HCl |
| KHG26813 | H | $C_6H_4$(2-$CH_3$) | $C_6H_3$(3-F,4-Cl) | HCl |
| KHG26814 | H | $C_6H_4$(3-$CH_3$) | $C_6H_3$(3-F,4-Cl) | HCl |
| KHG26815 | H | $C_6H_4$(4-$CH_3$) | $C_6H_3$(3-F,4-Cl) | HCl |
| KHG26816 | H | $C_6H_4$(2-Cl) | $C_6H_3$(3-F,4-Cl) | HCl |
| KHG26817 | H | $C_6H_4$(3-Cl) | $C_6H_3$(3-F,4-Cl) | HCl |
| KHG26818 | H | $C_6H_4$(4-Cl) | $C_6H_3$(3-F,4-Cl) | HCl |
| KHG26819 | H | $C_6H_4$(2-$OCF_3$) | $C_6H_3$(3-F,4-Cl) | HCl |
| KHG26820 | H | $C_6H_4$(3-$OCF_3$) | $C_6H_3$(3-F,4-Cl) | HCl |
| KHG26821 | H | $C_6H_4$(4-$OCF_3$) | $C_6H_3$(3-F,4-Cl) | HCl |
| KHG26822 | H | $C_6H_3$(3,4-di F) | $C_6H_3$(3-F,4-Cl) | HCl |
| KHG26823 | H | $C_6H_3$(3,4-di Cl) | $C_6H_3$(3-F,4-Cl) | HCl |
| KHG26878 | H | $CH_2C_6H_5$ | $C_6H_3$(3-F,4-Cl) | HCl |
| KHG26879 | H | $COC_6H_5$ | $C_6H_3$(3-F,4-Cl) | HCl |
| KHG26890 | H | $C_6H_5$ | $C_6H_3$(3-Cl,4-F) | HCl |
| KHG26891 | H | $C_6H_4$(2-F) | $C_6H_3$(3-Cl,4-F) | HCl |
| KHG26892 | H | $C_6H_4$(3-F) | $C_6H_3$(3-Cl,4-F) | HCl |
| KHG26893 | H | $C_6H_4$(4-F) | $C_6H_3$(3-Cl,4-F) | HCl |
| KHG26894 | H | $C_6H_4$(2-Cl) | $C_6H_3$(3-Cl,4-F) | HCl |
| KHG26895 | H | $C_6H_4$(3-Cl) | $C_6H_3$(3-Cl,4-F) | HCl |
| KHG26896 | H | $C_6H_4$(4-Cl) | $C_6H_3$(3-Cl,4-F) | HCl |
| KHG26897 | H | $C_6H_4$(2-$CH_3$) | $C_6H_3$(3-Cl,4-F) | HCl |
| KHG26898 | H | $C_6H_4$(3-$CH_3$) | $C_6H_3$(3-Cl,4-F) | HCl |
| KHG26899 | H | $C_6H_4$(4-$CH_3$) | $C_6H_3$(3-Cl,4-F) | HCl |
| KHG26900 | H | $C_6H_4$(2-$OCF_3$) | $C_6H_3$(3-Cl,4-F) | HCl |
| KHG26901 | H | $C_6H_4$(3-$OCF_3$) | $C_6H_3$(3-Cl,4-F) | HCl |
| KHG26902 | H | $C_6H_3$(3,4-di F) | $C_6H_3$(3-Cl,4-F) | HCl |
| KHG26903 | H | $C_6H_3$(3,4-di Cl) | $C_6H_3$(3-Cl,4-F) | HCl |
| KHG27252 | H | $C_4H_{10}$ | $C_6H_3$(3,4-di Cl) | HCl |
| KHG27253 | H | $C_4H_7$ | $C_6H_3$(3,4-di Cl) | HCl |
| KHG27254 | H | $C_5H_9$ | $C_6H_3$(3,4-di Cl) | HCl |
| KHG27255 | H | $C_6H_{11}$ | $C_6H_3$(3,4-di Cl) | HCl |
| KHG27279 | H | tetrazoyl($C_1H_1N_4$) | $C_{10}H_7$ | HCl |
| KHG27280 | H | Tetrazoly | $C_6H_3$(3,4-di Cl) | HCl |
| KHG27281 | H | Tetrazoyl | $C_6H_3$(3-Cl,4-F) | HCl |
| KHG27282 | H | tetrazoyl | $C_6H_3$(3,4-di F) | HCl |
| KHG27284 | H | $C_{10}H_7$ | $CH_2CH_2CH_3$ | HCl |
| KHG27270 | H | $CH_2CH_2CH_3$ | $C_6H_3$(3,4-di F) | HCl |
| KHG27271 | H | $C_6H_4$(2-F) | $C_6H_3$(3,4-di F) | HCl |
| KHG27273 | H | $C_6H_4$(4-F) | $C_6H_3$(3,4-di F) | HCl |
| KHG27274 | H | $C_6H_4$(2-Cl) | $C_6H_3$(3,4-di F) | HCl |
| KHG27275 | H | $C_6H_4$(3-Cl) | $C_6H_3$(3,4-di F) | HCl |
| KHG27276 | H | $C_6H_4$(2-$CH_3$) | $C_6H_3$(3,4-di F) | HCl |
| KHG27277 | H | $C_6H_4$(3-$CH_3$) | $C_6H_3$(3,4-di F) | HCl |
| KHG27278 | H | $C_6H_4$(4-$CH_3$) | $C_6H_3$(3,4-di F) | HCl |
| KHG27285 | H | $C_{10}H_7$ | $C_6H_5$ | HCl |
| KHG26906 | $CH_3$ | $C_6H_5$ | $C_6H_3$(3,4-di Cl) | — |
| KHG26907 | $CH_3$ | $C_6H_5$ | $C_{10}H_7$ | — |

Experimental Example 1

Neurotransporter Binding Assay 1. hSERT Binding Assay

5-HT transporter binding assay for evaluating binding of the compound to the serotonin transporter was carried out using human recombinant serotonin transporter membrane (PerkinElmer Life and Analytical Sciences, USA) expressed in HEK293 cells and radioisotope [$^3$H]Imipramine (PerkinElmer).

That is, the test drug, 2 nM [$^3$H]Imipramine, serotonin transporter membrane (9 ug/well), 120 mM NaCl and 50 mM Tris-HCl buffer (pH 7.4) containing 5 mM KCl were added to obtain a reaction mixture with a final volume of 0.25 ml. After incubation for 30 minutes at 27° C., the mixture was quickly passed through a Filtermat A glass fiber filter (PerkinElmer) pre-soaked with 0.5% (w/v) PEI (polyethyleneimine) using Inotech Harvester (Inotech) to terminate the reaction. After washing with cold washing buffer (50 mM Tris-HCl, pH 7.4, 154 mM NaCl) solution, the filter was covered with MeltiLex and sealed in a sample bag. After drying in an oven, radioactivity was counted using MicroBeta Plus (Wallac).

Non-specific binding was measured in the presence of 200 uM imipramine (Sigma). The $IC_{50}$ value of the test drug was calculated from non-linear regression analysis (GraphPad Prism Program, San Diego, USA) of each %-inhibition value obtained from the drug with concentrations of 7th and 8th steps.

2. hNET Binding Assay

NE transporter binding assay for evaluating binding of the compound to the norepinephrine transporter was carried out using human recombinant norepinephrine transporter membrane (PerkinElmer Life and Analytical Sciences, USA) expressed in MDCK cells and radioisotope [$^3$H]Nisoxetine (PerkinElmer).

That is, the test drug, 6 nM [$^3$H]Nisoxetine, norepinephrine transporter membrane (11 ug/well), 120 mM NaCl and 50 mM Tris-HCl buffer (pH 7.4) containing 5 mM KCl were added to obtain a reaction mixture with a final volume of 0.25 ml. After incubation for 60 minutes at 4° C., the mixture was quickly passed through a Filtermat A glass fiber filter pre-soaked with 0.5% (w/v) PEI (polyethyleneimine) using Inotech Harvester (Inotech) to terminate the reaction. After washing with cold washing buffer (50 mM Tris-HCl, pH 7.4, 0.9% NaCl) solution, the filter was covered with MeltiLex and sealed in a sample bag. After drying in an oven, radioactivity was counted using MicroBeta Plus (Wallac).

Non-specific binding was measured in the presence of 1 uM desipramine. The $IC_{50}$ value of the test drug was calculated from non-linear regression analysis (GraphPad Prism Program, San Diego, USA) of each %-inhibition value obtained from the drug with concentrations of 7th and 8th steps.

3. hDAT Binding Assay

DA transporter binding assay for evaluating binding of the compound to the dopamine transporter was carried out using human recombinant dopamine transporter membrane (PerkinElmer Life and Analytical Sciences, USA) expressed in CHO-K1 cells and radioisotope [$^3$H]WIN35,428 (PerkinElmer).

That is, the test drug, 8 nM [$^3$H]WIN35,428, dopamine transporter membrane (23 ug/well), and 50 mM Tris-HCl buffer (pH 7.4) containing 100 mM NaCl were added to obtain a reaction mixture with a final volume of 0.25 ml. After incubation for 120 minutes at 4° C., the mixture was quickly passed through a Filtermat A glass fiber filter pre-soaked with 0.5% (w/v) PEI (polyethyleneimine) using Inotech Harvester (Inotech) to terminate the reaction. After washing with cold washing buffer (50 mM Tris-HCl, pH 7.4, 0.9% NaCl) solution, the filter was covered with MeltiLex and sealed in a sample bag. After drying in an oven, radioactivity was counted using MicroBeta Plus (Wallac).

Non-specific binding was measured in the presence of 10 uM GBR-12909. The $IC_{50}$ value of the test drug was calculated from non-linear regression analysis (GraphPad Prism Program, San Diego, USA) of each %-inhibition value obtained from the drug with concentrations of 7th and 8th steps.

The result of the neurotransporter binding assay thus obtained was compared with the standard Fluoxetine, and shown in the following Table 2.

TABLE 2

Result of neurotransporter binding assay

| Compound No. | hSERT binding assay | | hNET binding assay | | hDAT binding assay | |
|---|---|---|---|---|---|---|
| | %-inhibition (10 uM) | IC50 (nM) | %-inhibition (10 uM) | IC50 (nM) | %-inhibition (10 uM) | IC50 (nM) |
| Fluoxetine | <50 | 3.58 | 79 | 2535 | 49 | >10000 |
| KHG26753 | 95 | 42.9 | 52 | — | 58 | — |
| KHG26754 | 95 | 120.0 | 91 | 666.0 | 76 | 1950 |
| KHG26756 | 79 | 271.0 | 85 | 339.0 | 54 | — |
| KHG26757 | 83 | 97.5 | 86 | 153.0 | 58 | — |
| KHG26765 | 98 | 112.0 | 90 | 1660.0 | 87 | 857 |
| KHG26766 | 98 | 9.2 | 90 | 90.2 | 94 | 227 |
| KHG26767 | 98 | 4.3 | 100 | 5.5 | 94 | 68.8 |
| KHG26768 | 97 | 82.9 | 84 | 2299 | 90 | 985 |
| KHG26769 | 100 | 21.6 | 94 | 1344 | 84 | 290 |
| KHG26770 | 98 | 7.81 | 99 | 93.1 | 96 | 23.2 |
| KHG26771 | 92 | 402 | 54 | — | 77 | 1683 |
| KHG26772 | 96 | 357 | 90 | 3475 | 66 | 319 |
| KHG26773 | 100 | 69.9 | 100 | 214 | 97 | 241 |
| KHG26774 | 100 | 11.6 | 100 | 25.8 | 96 | 119 |
| KHG26775 | 99 | 19.8 | 100 | 28.4 | 99 | 61.8 |
| KHG26776 | 100 | 5.67 | 100 | 27.1 | 95 | 168 |

As shown in Table 2, it was found that the conventional antidepressant, Fluoxetine showed inhibitory effect on a part of the three types of neurotransporters, and showed no inhibitory effect on all of the three types of neurotransporters, whereas the compound of the present invention showed inhibitory effect on all of the three types of neurotransporters at the same time.

Experimental Example 2

Neurotransporter Reuptake Inhibitory Assay

Reuptake inhibitory activity of the synthesized compound against the neurotransporters was tested in vitro. This activity means an ability of the synthesized compound to block the reuptake of neurotransmitters through three types of the monoamine neurotransporters, dopamine, norepinephrine, and serotonin transporters. In order to perform cell-based screening for candidate inhibitors of dopamine, norepinephrine, and serotonin reuptake, a real-time fluorescence monitoring system, high-throughput screening system (FDSS6000 (Functional Drug Screening System 6000)) was used. In this Experimental Example, HEK293 cell lines (HEK-hDAT, HEK-hNET, HEK-hSERT) that expressed human dopamine, norepinephrine, and serotonin transporters, respectively were treated with the inhibitors, and then intracellular changes in the monoamine neurotransmitters were measured to determine $IC_{50}$ values.

Cell Culture and Preparation

Activity of the synthesized compound was tested using HEK293 cell lines (HEK-hDAT, HEK-hNET, HEK-hSERT; University of North Carolina-Chapel Hill, provided by professor Bryan Roth), in which Human dopamine, norepinephrine, and serotonin transporters were stably expressed, respectively.

HEK293 cells, in which each transporter was stably expressed, were cultured in Dulbecco's modified Eagle's medium (Welgene, Daegu, Korea) containing 10% (v/v) fetal bovine serum, penicillin (100 U/ml), and streptomycin (100 μg/ml) in an incubator of 37° C., 5% carbon dioxide with humidity conditions and subcultured every 3-4 days.

In order to select cells expressing each transporter, HEK-hDAT cell line, HEK-hNET cell line, and HEK-hSERT cell line were treated with 350 mg/ml, 200 mg/ml, and 500 mg/ml of Geneticin G418 (Gibco, USA), respectively and cultured (in an incubator of 37° C., 5% carbon dioxide with humidity conditions). Cells were placed in a 96-well plate (NUNC, Rochester, N.Y., USA) coated with poly-L-lysine (0.05 mg/ml) at a density of $5 \times 10^4$ cells per well at 18-20 hours before the activity of the monoamine reuptake inhibitor compound was screened using FDSS6000 device (Hamamatsu Photonics, Hamamatsu, Japan).

Measurement Using High-Throughput Screening System FDSS6000 and Data Analysis

Reuptake inhibitory activity was measured after treatment of the inhibitor using a neurotransmitter transporter uptake assay kit (Molecular Devices, Sunnyvale, Calif., USA) including a fluorescent indicator that mimics DA (dopamine), NE (norepinephrine), and 5-HT (serotonin), and the intracellular reuptake of the indicator was measured by fluorescent signals. The indicator included in the kit was used. The indicator that mimics dopamine, norepinephrine, and serotonin and is labeled with a fluorescent dye is included in the powdery form in the assay kit. This indicator was dissolved in HEPES buffer, and used in the experiment. One type of indicator is included in the assay kit, and all indicators used in the experiment of dopamine, norepinephrine, and serotonin reuptake were the same indicator.

On the day of experiment, adherent cells in the 96-well plate were washed with a HEPES buffer solution (unit mM: 150 NaCl, 5 KCl, 2 $CaCl_2$, 1 $MgCl_2$, 10 Glucose, 10 HEPES, pH 7.4) using a self-maintaining 96-well plate washer ELx405 Select CW (BioTek Instruments, Winooski, Vt., USA) three times, and then a dye solution prepared according to the manufacturer's instructions was added to immediately measure fluorescence intensity. Reuptake of the fluorescent-labeled indicator was measured by changes in the fluorescence intensity according to intracellular concentration of the indicator using FDSS6000 device (Hamamatsu Photonics, Hamamatsu, Japan) for 30 minutes.

Intracellular changes in the fluorescence intensity were calculated from the final fluorescence intensity (Endpoint) that was measured at 30 minutes after initiation of the measurement of fluorescence intensity. For detailed fluorescence imaging technology, cells were selectively exposed to 440 nm light excited by 4 xenon lamps installed in FDSS6000 using a computer-controlled filter wheel. The emitter fluorescence light through a 515 nm long-pass filter was passed by a freezing digital CCD camera mounted on the device, and measured at 520 nm every 10 seconds using a digital fluorescent analyzer.

In the experiment for measuring the inhibitory effect, cells were pre-treated with the test drug in an incubator of 37° C., 5% carbon dioxide with humidity conditions for 15 minutes, and the dye solution prepared according to the manufacturer's instructions was added thereto. After addition of the dye solution to cells, fluorescence intensity was immediately measured. Intracellular change in the fluorescence intensity was measured for 30 minutes to obtain the final fluorescence intensity (Endpoint).

The final fluorescence intensity (Endpoint) of the control group treated with no test substance was regarded as 100%, and % inhibition rate of the test substance (% of control) was calculated to give a dose-response curve, and $IC_{50}$ value was calculated from a fitted Hill equation using GraphPad Prism4 (GraphPad Software, La Jolla, Calif., USA) program. GBR12909, Nisoxetine and Fluoxetine (Tocris Bioscience, Ellisville, Mo., USA) were used as control drugs for hDAT, hNET, and hSERT, respectively. All image data and analyses were obtained by using FDSS6000-exclusive program provide by Hamamatsu Photonics (Hamamatsu, Japan).

The result of neurotransmitter reuptake assay thus obtained was compared with the standard Fluoxetine, and shown in the following Tables 3 and 4.

TABLE 3

Result of neurotransmitter reuptake assay

| Compound No. | hSERT reuptake assay IC50 (uM) | hNET reuptake assay IC50 (uM) | hDAT reuptake assay IC50 (uM) |
|---|---|---|---|
| Fluoxetine | 0.15 | 4.41 | 18.4 |
| KHG26765 | 0.05 | 0.04 | 0.38 |
| KHG26766 | 0.04 | 0.04 | 0.15 |
| KHG26767 | 0.05 | 0.03 | 0.06 |
| KHG26768 | 4.6 | 0.8 | 1.9 |
| KHG26769 | 1.5 | 0.5 | 0.8 |
| KHG26770 | 0.9 | 0.7 | 0.8 |
| KHG26772 | 2.6 | 2.5 | 1.3 |
| KHG26773 | 0.9 | 1.1 | 0.5 |
| KHG26774 | 0.8 | 2.2 | 0.3 |
| KHG26775 | 0.6 | 0.6 | 0.4 |
| KHG26776 | 0.7 | 0.5 | 0.3 |

TABLE 4

Result of neurotransmitter reuptake assay

| Compound No. | hSERT reuptake assay IC50 (nM) | hNET reuptake assay IC50 (nM) | hDAT reuptake assay IC50 (nM) |
|---|---|---|---|
| Fluoxetine | 120.0 | 9630.0 | 23950.0 |
| KHG27252 | 86.96 | 95.98 | 100.35 |
| KHG27253 | 25.56 | 11.00 | 33.41 |
| KHG27254 | 25.77 | 15.83 | 25.79 |
| KHG27255 | 58.39 | 14.23 | 54.79 |
| KHG27284 | 8.55 | 79.48 | 710.3 |
| KHG26907 | 201.87 | 87.86 | 222.63 |

As shown in Tables 3 and 4, it was found that the conventional antidepressant, Fluoxetine showed excellent inhibitory activity against serotonin reuptake, but showed no great inhibitory activity against reuptake of other two types of neurotransmitters, whereas the compound of the present invention showed excellent inhibitory activity against reuptake of all of the three types of neurotransporters at the same time.

What is claimed is:

1. A compound having the structure of Chemical Formula 1 or a pharmaceutically acceptable salt thereof:

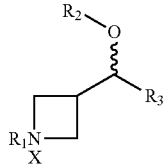

[Chemical Formula 1]

wherein $R_1$ is hydrogen or a methyl group,
$R_2$ is hydrogen, a naphthyl group, a straight- or branched-chain alkyl group having 1 to 5 carbon atoms, —$COC_6H_5$, or a substituted or unsubstituted phenyl group or benzyl group, in which one or more hydrogen atoms of the substituted phenyl group or benzyl group are each independently substituted with one selected from the group consisting of halogen, a straight- or branched-chain alkyl group having 1 to 3 carbon atoms, and trifluoromethoxy,
$R_3$ is a straight- or branched-chain alkyl group having 4 to 5 carbon atoms, a tetrazole group, a cyclic alkyl group having 3 to 10 carbon atoms, or a substituted or unsubstituted aromatic compound having 6 to 12 carbon atoms, in which one or more hydrogen atoms of the substituted aromatic compound are each independently substituted with one selected from the group consisting of halogen and a straight- or branched-chain alkyl group having 1 to 3 carbon atoms, and
X is hydrogen halide or does not exist.

2. The compound or the pharmaceutically acceptable salt thereof according to claim 1, wherein $R_1$ is hydrogen,
$R_2$ is hydrogen, a naphthyl group, a straight- or branched-chain alkyl group having 1 to 3 carbon atoms, —$COC_6H_5$, or a substituted or unsubstituted phenyl group or benzyl group, in which one or two hydrogen atoms of the substituted phenyl group or benzyl group is/are each independently substituted with one selected from the group consisting of fluorine, chlorine, methyl, and trifluoromethoxy,
$R_3$ is a straight- or branched-chain alkyl group having 4 to 5 carbon atoms, a tetrazole group, a cyclic alkyl group having 3 to 6 carbon atoms, or a substituted or unsubstituted phenyl or naphthyl group, in which one or two hydrogen atoms of the substituted phenyl or naphthyl group is/are each independently substituted with one selected from the group consisting of fluorine, chlorine, and methyl, and
X is hydrogen chloride or does not exist.

3. The compound or the pharmaceutically acceptable salt thereof according to claim 1, wherein $R_1$, $R_2$, $R_3$, and X are the same as in Table 5.

TABLE 5

| $R_1$ | $R_2$ | $R_3$ | X |
|---|---|---|---|
| H | H | $C_6H_5$ | HCl |
| H | $CH_3$ | $C_6H_5$ | HCl |
| H | $CH_2CH_3$ | $C_6H_5$ | HCl |

TABLE 5-continued

| R₁ | R₂ | R₃ | X |
|---|---|---|---|
| H | H | C₆H₄(4-Cl) | HCl |
| H | CH₃ | C₆H₄(4-Cl) | HCl |
| H | CH₂CH₃ | C₆H₄(4-Cl) | HCl |
| H | H | C₆H₃(3,4-di Cl) | HCl |
| H | CH₃ | C₆H₃(3,4-di Cl) | HCl |
| H | CH₂CH₃ | C₆H₃(3,4-di Cl) | HCl |
| H | H | CH₂C₆H₅ | HCl |
| H | CH₃ | C₆H₄(2-Me) | HCl |
| H | C₆H₅ | C₆H₅ | HCl |
| H | C₆H₅ | C₆H₄(4-Cl) | HCl |
| H | C₆H₅ | C₆H₃(3,4-di Cl) | HCl |
| H | CH₂C₆H₅ | C₆H₅ | HCl |
| H | CH₂C₆H₅ | C₆H₄(4-Cl) | HCl |
| H | CH₂C₆H₅ | C₆H₃(3,4-di Cl) | HCl |
| H | COC₆H₅ | C₆H₅ | HCl |
| H | COC₆H₅ | C₆H₄(4-Cl) | HCl |
| H | COC₆H₅ | C₆H₃(3,4-di Cl) | HCl |
| H | C₆H₄(2-CH₃) | C₆H₃(3,4-di Cl) | HCl |
| H | C₆H₄(3-CH₃) | C₆H₃(3,4-di Cl) | HCl |
| H | C₆H₄(4-CH₃) | C₆H₃(3,4-di Cl) | HCl |
| H | CH₂CH₂CH₃ | C₆H₃(3,4-di Cl) | HCl |
| H | C₆H₄(2-F) | C₆H₃(3,4-di Cl) | HCl |
| H | C₆H₄(3-F) | C₆H₃(3,4-di Cl) | HCl |
| H | C₆H₄(4-F) | C₆H₃(3,4-di Cl) | HCl |
| H | C₆H₄(2-Cl) | C₆H₃(3,4-di Cl) | HCl |
| H | C₆H₄(3-Cl) | C₆H₃(3,4-di Cl) | HCl |
| H | C₆H₄(4-Cl) | C₆H₃(3,4-di Cl) | HCl |
| H | C₆H₄(2-OCF₃) | C₆H₃(3,4-di Cl) | HCl |
| H | C₆H₄(3-OCF₃) | C₆H₃(3,4-di Cl) | HCl |
| H | C₆H₄(4-OCF₃) | C₆H₃(3,4-di Cl) | HCl |
| H | C₆H₃(3,4-di F) | C₆H₃(3,4-di Cl) | HCl |
| H | C₆H₃(3,4-di Cl) | C₆H₃(3,4-di Cl) | HCl |
| H | CH₂CH₃ | C₁₀H₇ | HCl |
| H | CH₂CH₂CH₃ | C₁₀H₇ | HCl |
| H | C₆H₅ | C₁₀H₇ | HCl |
| H | C₆H₄(2-F) | C₁₀H₇ | HCl |
| H | C₆H₄(3-F) | C₁₀H₇ | HCl |
| H | C₆H₄(4-F) | C₁₀H₇ | HCl |
| H | C₆H₄(2-CH₃) | C₁₀H₇ | HCl |
| H | C₆H₄(3-CH₃) | C₁₀H₇ | HCl |
| H | C₆H₄(4-CH₃) | C₁₀H₇ | HCl |
| H | C₆H₄(2-Cl) | C₁₀H₇ | HCl |
| H | C₆H₄(3-Cl) | C₁₀H₇ | HCl |
| H | C₆H₄(4-Cl) | C₁₀H₇ | HCl |
| H | C₆H₄(2-OCF₃) | C₁₀H₇ | HCl |
| H | C₆H₄(3-OCF₃) | C₁₀H₇ | HCl |
| H | C₆H₄(4-OCF₃) | C₁₀H₇ | HCl |
| H | C₆H₃(3,4-F) | C₁₀H₇ | HCl |
| H | C₆H₃(3,4-di Cl) | C₁₀H₇ | HCl |
| H | CH₂CH₃ | C₆H₃(3-F,4-Cl) | HCl |
| H | C₆H₅ | C₆H₃(3-F,4-Cl) | HCl |
| H | C₆H₄(2-F) | C₆H₃(3-F,4-Cl) | HCl |
| H | C₆H₄(3-F) | C₆H₃(3-F,4-Cl) | HCl |
| H | C₆H₄(4-F) | C₆H₃(3-F,4-Cl) | HCl |
| H | C₆H₄(2-CH₃) | C₆H₃(3-F,4-Cl) | HCl |
| H | C₆H₄(3-CH₃) | C₆H₃(3-F,4-Cl) | HCl |
| H | C₆H₄(4-CH₃) | C₆H₃(3-F,4-Cl) | HCl |
| H | C₆H₄(2-Cl) | C₆H₃(3-F,4-Cl) | HCl |
| H | C₆H₄(3-Cl) | C₆H₃(3-F,4-Cl) | HCl |
| H | C₆H₄(4-Cl) | C₆H₃(3-F,4-Cl) | HCl |
| H | C₆H₄(2-OCF₃) | C₆H₃(3-F,4-Cl) | HCl |
| H | C₆H₄(3-OCF₃) | C₆H₃(3-F,4-Cl) | HCl |
| H | C₆H₄(4-OCF₃) | C₆H₃(3-F,4-Cl) | HCl |
| H | C₆H₃(3,4-di F) | C₆H₃(3-F,4-Cl) | HCl |
| H | C₆H₃(3,4-di Cl) | C₆H₃(3-F,4-Cl) | HCl |
| H | CH₂C₆H₅ | C₆H₃(3-F,4-Cl) | HCl |
| H | COC₆H₅ | C₆H₃(3-F,4-Cl) | HCl |
| H | C₆H₅ | C₆H₃(3-Cl,4-F) | HCl |
| H | C₆H₄(2-F) | C₆H₃(3-Cl,4-F) | HCl |
| H | C₆H₄(3-F) | C₆H₃(3-Cl,4-F) | HCl |
| H | C₆H₄(4-F) | C₆H₃(3-Cl,4-F) | HCl |
| H | C₆H₄(2-Cl) | C₆H₃(3-Cl,4-F) | HCl |
| H | C₆H₄(3-Cl) | C₆H₃(3-Cl,4-F) | HCl |
| H | C₆H₄(4-Cl) | C₆H₃(3-Cl,4-F) | HCl |
| H | C₆H₄(2-CH₃) | C₆H₃(3-Cl,4-F) | HCl |
| H | C₆H₄(3-CH₃) | C₆H₃(3-Cl,4-F) | HCl |
| H | C₆H₄(4-CH₃) | C₆H₃(3-Cl,4-F) | HCl |
| H | C₆H₄(2-OCF₃) | C₆H₃(3-Cl,4-F) | HCl |
| H | C₆H₄(3-OCF₃) | C₆H₃(3-Cl,4-F) | HCl |
| H | C₆H₃(3,4-di F) | C₆H₃(3-Cl,4-F) | HCl |
| H | C₆H₃(3,4-di Cl) | C₆H₃(3-Cl,4-F) | HCl |
| H | C₄H₁₀ | C₆H₃(3,4-di Cl) | HCl |
| H | C₄H₇ | C₆H₃(3,4-di Cl) | HCl |
| H | C₅H₉ | C₆H₃(3,4-di Cl) | HCl |
| H | C₆H₁₁ | C₆H₃(3,4-di Cl) | HCl |
| H | C₁H₁N₄ | C₁₀H₇ | HCl |
| H | C₁H₁N₄ | C₆H₃(3,4-di Cl) | HCl |
| H | C₁H₁N₄ | C₆H₃(3-Cl,4-F) | HCl |
| H | C₁H₁N₄ | C₆H₃(3,4-di F) | HCl |
| H | C₁₀H₇ | CH₂CH₂CH₃ | HCl |
| H | CH₂CH₂CH₃ | C₆H₃(3,4-di F) | HCl |
| H | C₆H₄(2-F) | C₆H₃(3,4-di F) | HCl |
| H | C₆H₄(4-F) | C₆H₃(3,4-di F) | HCl |
| H | C₆H₄(2-Cl) | C₆H₃(3,4-di F) | HCl |
| H | C₆H₄(3-Cl) | C₆H₃(3,4-di F) | HCl |
| H | C₆H₄(2-CH₃) | C₆H₃(3,4-di F) | HCl |
| H | C₆H₄(3-CH₃) | C₆H₃(3,4-di F) | HCl |
| H | C₆H₄(4-CH₃) | C₆H₃(3,4-di F) | HCl |
| H | C₁₀H₇ | C₆H₅ | HCl |
| CH₃ | C₆H₅ | C₆H₃(3,4-di Cl) | — |
| CH₃ | C₆H₅ | C₁₀H₇ | —. |

4. A pharmaceutical composition, comprising the compound or the pharmaceutically acceptable salt thereof of claim 1 as an active ingredient.

5. A pharmaceutical composition, comprising the compound or the pharmaceutically acceptable salt thereof of claim 2 as an active ingredient.

6. A pharmaceutical composition, comprising the compound or the pharmaceutically acceptable salt thereof of claim 3 as an active ingredient.

7. A method for treating depression or psychiatric disorders,
wherein the psychiatric disorder is neurogenic pain, mood disorders, sleep disorders, anxiety disorder, attention deficit hyperactive disorder (ADHD), or eating disorder, comprising the step of administering the compound having the structure of Chemical Formula 1 or the pharmaceutically acceptable salt thereof at a therapeutically effective amount to a patient in need:

[Chemical Formula 1]

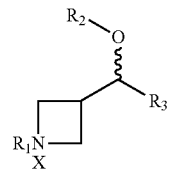

wherein $R_1$ is hydrogen or a methyl group,
$R_2$ is hydrogen, a naphthyl group, a straight- or branched-chain alkyl group having 1 to 5 carbon atoms, —COC₆H₅, or a substituted or unsubstituted phenyl group or benzyl group, in which one or more hydrogen atoms of the substituted phenyl group or benzyl group are each independently substituted with one selected from the group consisting of halogen, a straight- or branched-chain alkyl group having 1 to 3 carbon atoms, and trifluoromethoxy,
$R_3$ is a straight- or branched-chain alkyl group having 3 to 5 carbon atoms, a tetrazole group, a cyclic alkyl group having 3 to 10 carbon atoms, or a substituted or unsubstituted aromatic compound having 6 to 12 carbon atoms, in which one or more hydrogen atoms of the substituted aromatic compound are each independently substituted with one selected from the group consisting of halogen and a straight- or branched-chain alkyl group having 1 to 3 carbon atoms, and X is hydrogen halide or does not exist.

8. A method for treating depression or psychiatric disorders, wherein the psychiatric disorder is neurogenic pain, mood disorders, sleep disorders, anxiety disorder, attention deficit hyperactive disorder (ADHD), or eating disorder, comprising the step of administering the compound or the pharmaceutically acceptable salt thereof of claim 2 at a therapeutically effective amount to a patient in need.

9. A method for treating depression or psychiatric disorders, wherein the psychiatric disorder is neurogenic pain, mood disorders, sleep disorders, anxiety disorder, attention deficit hyperactive disorder (ADHD), or eating disorder, comprising the step of administering the compound or the pharmaceutically acceptable salt thereof of claim 3 at a therapeutically effective amount to a patient in need.

* * * * *